United States Patent
Isobe

(10) Patent No.: US 11,538,583 B2
(45) Date of Patent: Dec. 27, 2022

(54) CONTROLLING DEVICES TO ACHIEVE MEDICAL OUTCOMES

(71) Applicant: HITACHI HIGH-TECH SOLUTIONS CORPORATION, Tokyo (JP)

(72) Inventor: Takashi Isobe, Santa Clara, CA (US)

(73) Assignee: HITACHI HIGH-TECH SOLUTIONS CORPORATION, Tokyo (JP)

( * ) Notice: Subject to any disclaimer, the term of this patent is extended or adjusted under 35 U.S.C. 154(b) by 293 days.

(21) Appl. No.: 16/962,890

(22) PCT Filed: Jan. 26, 2018

(86) PCT No.: PCT/US2018/015402
§ 371 (c)(1),
(2) Date: Jul. 17, 2020

(87) PCT Pub. No.: WO2019/147257
PCT Pub. Date: Aug. 1, 2019

(65) Prior Publication Data
US 2021/0383921 A1   Dec. 9, 2021

(51) Int. Cl.
*G16H 40/67* (2018.01)
*G16H 10/60* (2018.01)
*G16H 20/00* (2018.01)

(52) U.S. Cl.
CPC ............. *G16H 40/67* (2018.01); *G16H 10/60* (2018.01); *G16H 20/00* (2018.01)

(58) Field of Classification Search
None
See application file for complete search history.

(56) References Cited

U.S. PATENT DOCUMENTS

| | | | |
|---|---|---|---|
| 11,200,967 B1* | 12/2021 | Jain | G16H 50/70 |
| 2008/0114808 A1* | 5/2008 | Morita | G16H 15/00 |
| 2012/0232930 A1* | 9/2012 | Schmidt | A61B 6/5217 705/3 |

(Continued)

OTHER PUBLICATIONS

International Search Report PCT/US2018/015402 dated Mar. 29, 2018.

*Primary Examiner* — Jonathan Ng
(74) *Attorney, Agent, or Firm* — Mattingly & Malur, PC

(57) ABSTRACT

In some examples, a computer system may receive medical records for a plurality of patients. The system may generate a plurality of data representations based on the medical records for the individual patients, each data representation representing at least a therapy performed and a quantified disability status of the individual patient. The system may select a subset of the data representations for which an improvement in the quantified disability status exceeds a threshold. Further, the system may receive patient information for a first patient and may generate a first data representation from the patient information. The system may compare the first data representation with the data representations in the subset to determine at least one therapy predicted to provide an improvement in the current quantified disability of the first patient. The system may send information related to the at least one therapy to a computing device.

20 Claims, 11 Drawing Sheets

(56) References Cited

U.S. PATENT DOCUMENTS

| | | | |
|---|---|---|---|
| 2013/0226612 A1* | 8/2013 | Carmeli | G06Q 10/04 |
| | | | 705/2 |
| 2014/0089004 A1* | 3/2014 | Frey | G06Q 10/04 |
| | | | 705/3 |
| 2014/0122389 A1* | 5/2014 | Riskin | G16H 70/00 |
| | | | 707/738 |
| 2014/0279746 A1* | 9/2014 | De Bruin | G16H 10/60 |
| | | | 706/46 |
| 2017/0199965 A1* | 7/2017 | Dekel | G16H 50/20 |
| 2017/0329917 A1* | 11/2017 | McRaith | G16H 40/67 |
| 2018/0300640 A1* | 10/2018 | Birnbaum | G16H 10/60 |
| 2020/0272919 A1* | 8/2020 | Haimson | G16H 50/20 |
| 2021/0110895 A1* | 4/2021 | Shriberg | G06F 40/20 |
| 2021/0151140 A1* | 5/2021 | Bates | G16H 50/20 |

* cited by examiner

CONTROLLING DEVICES TO ACHIEVE MEDICAL OUTCOMES

TECHNICAL FIELD

This disclosure relates to the technical field of applying machine learning to medical therapy.

BACKGROUND

Patients with debilitating illnesses and disabilities, such as stroke, brain disease and injuries, spinal cord injuries, certain cancers, heart disease, kidney disease, and so forth, may require several types of therapy for progressing toward a recovery. Examples of such therapies may include physical therapy, occupational therapy, speech therapy, specific training, and the like. However, as several different types of therapy may be required, determining the proper combination and frequencies of the therapies, and subsequently implementing the therapies may not always be performed optimally, which may delay or inhibit recovery for individual patients. In addition, historical medical information such as therapy and recovery records may vary as time passes. Accordingly, the combination of therapies most likely to be successful may change based on the changes in the patients and the historical information. Therefore, it may be difficult for medical personnel, hospitals, or other recovery sites to improve their performance for maximizing recovery of their patients.

SUMMARY

Implementations herein include arrangements and techniques for efficient machine learning to determine a therapy plan for a patient. As one example, a computer system may receive medical records for a plurality of patients. The system may generate a plurality of data representations based on the medical records for the individual patients, each data representation representing at least a therapy performed and a quantified disability status of the individual patient. The system may select a subset of the data representations for which an improvement in the quantified disability status exceeds a threshold. Further, the system may receive patient information for a first patient and may generate a first data representation from the patient information. The system may compare the first data representation with the data representations in the subset to determine at least one therapy predicted to provide an improvement in the current quantified disability of the first patient. The system may send information related to the at least one therapy to a computing device.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DESCRIPTION OF THE EMBODIMENTS

Figure 1:
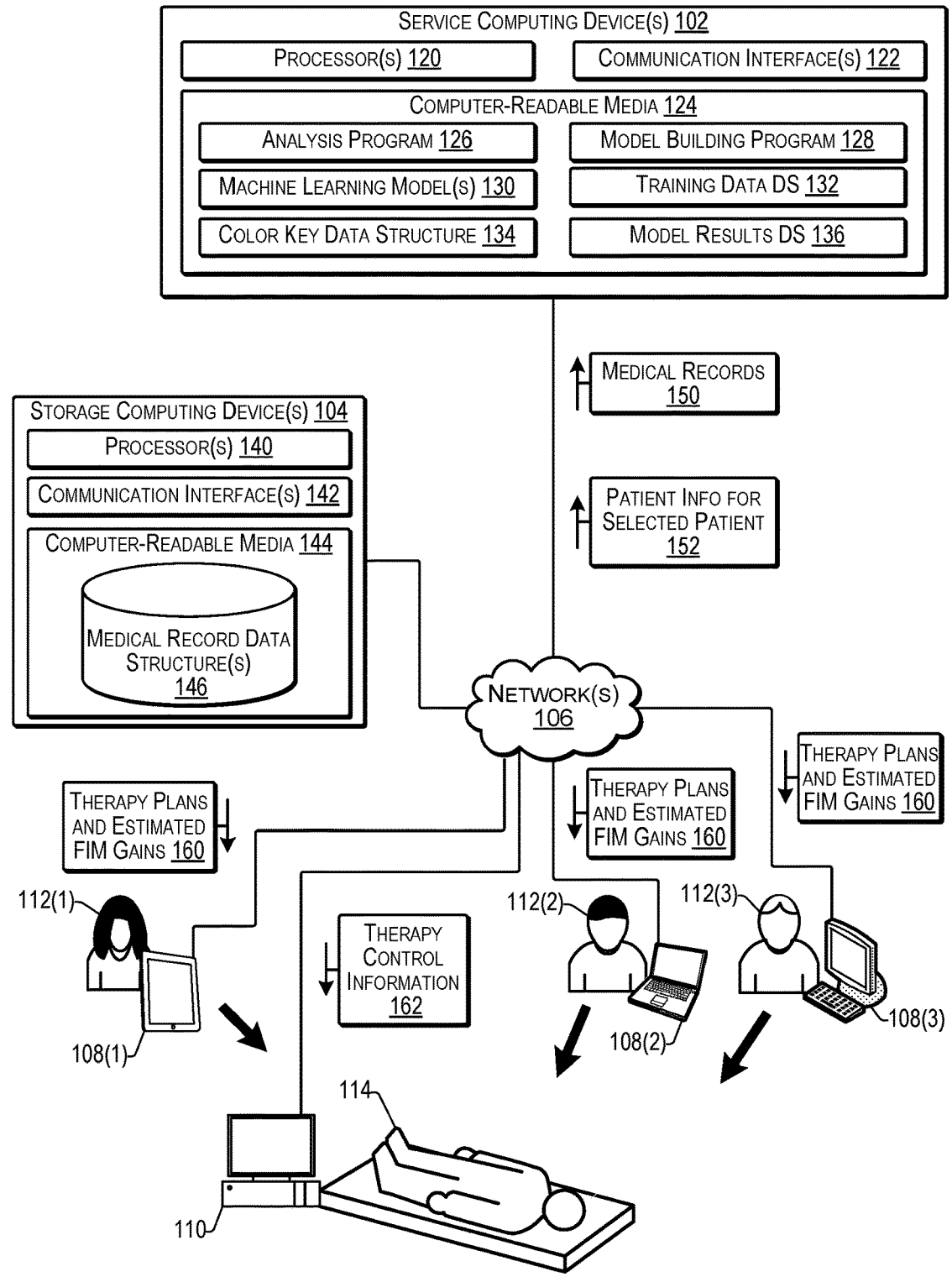
FIG. 1 illustrates an example architecture of a computer system able to determine and apply therapies according to some implementations.

Some implementations herein are directed to techniques and arrangements for determining and implementing a therapy plan based on analysis of time-series data for historical patient therapies and recoveries. The system may analyze medical data, such as may be obtained from one or more medical databases, or the like, and may select and/or implement a therapy plan for a selected patient based on the analysis. Some examples include use of an image-based data summation and representation technique that includes generating image-based data representations of time series medical data for use with a machine learning model that enables more efficient operation of the computer system than in conventional machine learning applications. The machine learning model may be trained using the image-based time-series data and may then be used to determine, for a particular patient, a selected therapy plan having a predicted improvement in disability condition. For instance, by generating image-based representations of time-series data from a medical record database for training the machine learning model, the system may subsequently use the machine learning model with an image-based representation of patient data of a selected patient as input for determining an optimal therapy plan from multiple possible therapy plan options for maximizing the recovery of the patient. Additionally, in other examples herein, the data representations may be matrix-based data representations, rather than image-based data representations.

The therapy plans herein may be determined based on a combination of patient demographic information and historical patient medical information. For example, the patient demographic information may include patient age, sex, disability level, diseases, residence type, family type, address, etc., of each patient. Further, the historical medical information may include therapy and recovery records. For instance, historical therapy records may include the number of occupational therapy (OT) sessions per time period, the number of speech therapy (ST) sessions per time period, the number of physical therapy (PT) sessions per time period, the number of specific training sessions per time period, and so forth. In addition, historical recovery records may include present and past Functional Independence Measurement (FIM) scores of the patient. FIM is a scoring system for quantifying the physical and cognitive disabilities of a patient and is described additionally below. Furthermore, while FIM scoring is used in the examples herein as one technique for quantifying a disability status of a patient, other disability quantification techniques may be used in the examples herein. Accordingly, implementations are not limited to the use of FIM scoring.

Some examples include a machine learning model able to recognize patterns of diseases or other disabilities, and corresponding therapies, and able to determine a therapy having a largest probability for success based on information specific to the particular patient. For instance, a graphical user interface (GUI) may be presented on a client device to enable input of patient demographic information such as patient age, sex, disability level, diseases, residence type, family type, and address of the patient. In addition, the GUI may enable input or access to historical information for the patient, such as the therapy records of any physical therapy, occupational therapy, speech therapy, and specific training, as well as recovery records such as FIM scores or other quantified disability status of the patient determined over time. The system may further include, or may access, a medical record database or other medical record data structure to record the patient information.

An analysis program may execute on a service computing device and may generate at least one patient data representation representing the patient demographic information and the patient historical information. The analysis program may invoke (or may have previously invoked) a model building program that may access training data including a plurality of other data representations for generating a machine learning model using the plurality of other data representations for training the machine learning model. For example, the analysis program may access a medical records database and may use the historical medical records of a plurality of past patients for generating the plurality of other data representations. In some examples, each data representation may be an image that visually represents a summary of the medical records of individual patients. In other examples, each data representation may be a matrix of values that represent a summary of the medical records of patients. The analysis program may store the plurality of data representations in a training data data structure, and the model building program may access the training data data structure for training the machine learning model.

In some examples, the data representations generated from the medical records may include a plurality of columns (also referred to as pixel bands) of blocks (also referred to as pixels). Each column may corresponding to a different parameter associated with the medical data for a patient, such as age, sex, disease, disability level, number of therapy sessions per week (or other specified time period) of PT, OT, ST and/or specific training. The blocks in each column may be colored or may otherwise have a graphic effect applied that corresponds to a value determined for the corresponding parameter at a corresponding point in time. Thus, as one concrete example, each data representation may include plurality of columns of colored blocks in which the colors are representative of values for the corresponding parameters corresponding to each column. The system may include a color key data structure that correlates particular colors or other graphic effects to particular parameter values or ranges of parameter values for each patient information parameter represented in the data representation.

In addition, the analysis program may append multiple therapy patterns to the patient data representation generated for the selected patient by combining the data representation representing the patient's data with multiple possible therapy patterns to generate multiple time data representations for the selected patient. The machine learning model may receive the multiple data representations of the patient as input for determining an improvement in the disability status of the patient predicted for a particular therapy plan. The machine learning model may be used to determine multiple therapy options that may maximize the expected recovery based on the result of pattern recognition of the patient data representations determined using the machine learning model.

A client application on a client device may present a GUI that receives the results determined by the machine learning model from the analysis program. For example, the GUI may present a visual representation of the results to a user, such as a medical professional. In some cases, the results may be presented to multiple users, each of which may view the results in a respective GUI presented on a respective computing device. In some examples, when there are multiple therapy and recovery options available, the GUI may enable the multiple users to user the GUI to determine a selected therapy for the patient. As one example if the users are a physical therapist, an occupational therapist, and a speech therapist, the GUI may provide them with an interface for selecting a preferred therapy from among two or more presented therapy options that are predicted to have a similar likelihood of success. Additionally, or alternatively, in some cases, the therapy plan may be implemented automatically by the analysis program or other program based on the determined result, such as by sending a control signal to a therapy device, or the like.

In some examples, the client application executing on the client computing device may present, in the GUI, a visualization of the patient's improvement in disability status of the patient expected from a selected therapy plan. For example, the visualization may include a predicted improvement in the patient's FIM score due to the selected therapy plan, i.e., an "FIM gain" or other quantified gain or improvement in the disability status of the patient. Additionally, in some cases, multiple therapy options may be presented for and one or more may be selected by a user for maximizing the expected recovery based on the result of the pattern recognition performed by the machine learning model.

For discussion purposes, some example implementations are described in the environment of a computer system that generates image-based or matrix-based data representations for patients, and uses a machine learning model trained using other data representations to determine an optimal therapy plan for the patients. However, implementations herein are not limited to the particular examples provided, and may be extended to other types of machine learning, other environments of use, other system architectures, other applications, and so forth, as will be apparent to those of skill in the art in light of the disclosure herein.

FIG. 1 illustrates an example architecture of a computer system 100 able to determine and apply therapies according to some implementations. The system 100 includes at least one service computing device 102 that is able to communicate with a storage computing device 104 through one or more networks 106. In addition, the service computing device 102 may communicate with one or more client devices 108 and/or one or more therapeutic devices 110 through the one or more networks 106. In this example, a first user 112(1) is associated with a first client device 108(1), a second user 110(2) is associated with a second client device 108(2), and a third user 112(3) is associated with a third client device 108(3). Furthermore, a patient 114 is associated with the therapeutic device 110. For instance, each of the users 108 may be a medical professional responsible for administering therapy to the patient 114. Additionally, or alternatively, the therapeutic device 110 may be operable to deliver therapy to the patient 114 automatically.

In some examples, the one or more networks 106 may include a local area network (LAN), while in other examples, the one or more networks 106 may include a wide area network (WAN) such as the Internet. Thus, the one or more networks 106 may include a wired network including fiber optics, Ethernet, Fibre Channel; etc.; a wireless network, such as a cellular network; a local wireless network, such as Wi-Fi; short-range wireless communications, such as BLUETOOTH®; a direct wired connection, or any combination thereof. Accordingly, the one or more networks 106 may include both wired and/or wireless communication technologies. Components used for such communications can depend at least in part upon the type of network, the environment selected, or both.

In some implementations, the service computing device 102 may include one or more servers, personal computers, or other types of computing devices that may be embodied in any of a number of ways. For instance, in the case of a server, the programs, other functional components, and at least a portion of data storage may be implemented on at least one server, such as on a stand-alone server, a cluster of servers, a server farm or data center, a cloud-hosted computing service, and so forth, although other computer architectures may additionally or alternatively be used.

In the illustrated example, the service computing device 102 includes, or otherwise may have associated therewith, one or more processors 120, one or more communication interfaces 122, and one or more computer-readable media 124. Each processor 120 may be a single processing unit or a number of processing units, and may include single or multiple computing units, or multiple processing cores. The processor(s) 120 may be implemented as one or more central processing units, microprocessors, microcomputers, microcontrollers, digital signal processors, state machines, logic circuitries, and/or any devices that manipulate signals based on operational instructions. For instance, the processor(s) 120 may be one or more hardware processors and/or logic circuits of any suitable type specifically programmed or configured to execute the algorithms and processes described herein. The processor(s) 120 may be configured to fetch and execute computer-readable instructions stored in the computer-readable media 124, which can program the processor(s) 120 as specific machines to perform the functions described herein.

The computer-readable media 124 may include volatile and nonvolatile memory and/or removable and non-removable media implemented in any type of technology for storage of information such as computer-readable instructions, data structures, program modules, or other data. For example, the computer-readable media 124 may include, but is not limited to, RAM, ROM, EEPROM, flash memory or other memory technology, optical storage, solid state storage, magnetic tape, magnetic disk storage, RAID storage systems, object storage systems, storage arrays, network attached storage, storage area networks, cloud storage, or any other medium that can be used to store the desired information and that can be accessed by a computing device. Depending on the configuration of the service computing device 102, the computer-readable media 124 may be a tangible non-transitory medium to the extent that, when mentioned, non-transitory computer-readable media exclude media such as energy, carrier signals, electromagnetic waves, and/or signals per se. In some cases, the computer-readable media 124 may be at the same location as the service computing device 102, while in other examples, the computer-readable media 124 may be partially remote from the service computing device 102.

The computer-readable media 124 may be used to store any number of functional components that are executable by the processor(s) 120. In many implementations, these functional components comprise executable instructions and/or programs that are executable by the processor(s) 120 and that, when executed, specifically program the processor(s) 120 to perform the actions attributed herein to the service computing device 102. Functional components stored in the computer-readable media 124 may include the analysis program 126 and the model building program 128. The analysis program 126 may include one or more computer programs, computer-readable instructions, executable code, or portions thereof that are executable to cause the processor(s) 120 to perform the various tasks described herein. In the illustrated example, the analysis program 126 may include or may access the model building program 128 that may be invoked to generate and train the one or more machine learning models (MLMs) 130 using training data from the training data data structure 132. In addition, the analysis program 126 may further be executed to generate a plurality of data representations from medical records that may be used as training data and stored in the training data data structure 132, as discussed additionally below.

The model building program 128 may be an executable module of the analysis program 126, or a portion thereof. Alternatively, in other examples, the model building program 128 may be a separately executable stand-alone computer program that may be invoked by the analysis program 126. The model building program 128 may configure the one or more processors 120 to build and train at least one machine learning model 130 to be used for determining therapies. The analysis program 126 may subsequently apply the trained machine learning model 130 to newly received patient data for determining one or more therapies for respective the patient.

Additionally, the functional components in the computer-readable media 124 may include an operating system (not shown in FIG. 1) that may control and manage various functions of the service computing device 102. In some cases, the functional components may be stored in a storage portion of the computer-readable media 124, loaded into a local memory portion of the computer-readable media 124, and executed by the one or more processors 120. Numerous other software and/or hardware configurations will be apparent to those of skill in the art having the benefit of the disclosure herein.

In addition, the computer-readable media 124 may store data and data structures used for performing the functions and services described herein. For example, the computer-readable media 124 may store the one or more machine learning models 130, and may store the training data in the training data data structure 132 used for training the machine learning model(s) 130. Additional data and data structures that may be stored in the computer-readable media 124 include a color key data structure 134 and a model results data structure 136. For instance, the color key data structure may relate specific colors to specific values or ranges of values for parameters represented in the data representations herein. Additionally, the model results data structure 136 may store the results provided by the machine learning model in response to the input of patient data for selected patients.

The machine learning model 130 may be used by the analysis program 126 for determining one or more optimal therapy plans for a specified patient whose data is input to the machine learning model 130. Examples of the machine learning model 130 may include classification models such as random forest, support vector machines, or deep learning networks, such as a convolutional neural network. Additional examples of the machine learning model 130 may include predictive models, decision trees, regression models, such as linear regression models, stochastic models, such as Markov models and hidden Markov models, artificial neural networks, such as recurrent neural networks, and so forth. Accordingly, implementations herein are not limited to a particular type of machine learning model.

The service computing device(s) 102 may also include or maintain other functional components and data, which may include programs, drivers, etc., and the data used or generated by the functional components. Further, the service computing device(s) 102 may include many other logical, programmatic, and physical components, of which those described above are merely examples that are related to the discussion herein.

The communication interface(s) 122 may include one or more interfaces and hardware components for enabling communication with various other devices, such as over the one or more networks 106. Thus, the communication interfaces 122 may include, or may couple to, one or more ports that provide connection to the network(s) 106. For example, the communication interface(s) 122 may enable communication through one or more of a LAN (local area network), WAN (wide area network), the Internet, cable networks, cellular networks, wireless networks (e.g., Wi-Fi) and wired networks (e.g., fiber optic, Ethernet, Fibre Channel), direct connections, as well as short-range wireless communications, such as BLUETOOTH®, and the like, as additionally enumerated below.

Further, the storage computing device(s) 104 may include one or more processors 140, one or more communication interfaces 142, and one or more computer-readable media 144. In some examples, the storage computing device(s) 104 may have a hardware configuration similar to the service computing device(s) 102 discussed above and/or may be one of the service computing devices 102. For example, the one or more processors 140 may include any of the examples of processors 120 discussed above, the one or more communication interfaces 142 may include any of the examples of communication interfaces 122 discussed above, and the one or more computer-readable media 144 may include any of the examples of computer-readable media 124 discussed above. The storage computing device 104 may store or otherwise maintain a medical record data structure 146, such as a medical record database containing historical patient data, therapies applied to the respective patients, and results of the therapies. The storage computing device(s) 104 may be a single computing device, or a plurality of computing devices, and may be at a single location, such as a hospital, or at multiple locations, such as at multiple hospitals, data centers, research facilities, and so forth.

The storage computing device(s) 104 may execute a storage program (not shown in FIG. 1) that may receive and store new medical records for storage in the medical record data structure 146. In addition, the storage program may grant access to stored medical records to authorized users of the medical records, while restricting unauthorized users from access. In some examples, the analysis program 126 may access the medical record data structure 146 to retrieve medical records 150 for generating a plurality of data representations from the medical records to use as training data for training the machine learning model(s) 130, as discussed additionally below.

The client device(s) 108, and in some cases, the therapy device 110 may include configurations and hardware similar to those discussed above with respect to the computing devices 102 and 104, but with different functional components and different data. For instance, the client devices 108 may be any type of computing device able to communicate over a network including server computing devices, desktop computing devices, laptop computing devices, tablet computing devices, smart phone computing devices, wearable computing devices, and so forth. The client devices 108 may include one or more processors, one or more communication interfaces, and one or more computer readable media (not shown in FIG. 1, which may be used to execute a client application (not shown in FIG. 1), such as for presenting a GUI to the users 112 for submitting patient information and for viewing selected therapies determined for the patient 114.

In addition, the therapy device 110 may be any of a variety of automated therapy devices, such as a locomotion training device to automatically move one or more of the patient's body parts for a specified time period, an automated stretching device to automatically stretch a patient body part, an automated traction device to apply traction to the patient, an automated electrostimulation device, a therapy robot, and so forth. The therapy device may include a processor, communication interface(s), and computer-readable media, similar to the computing devices 102 and 104 discussed above.

As mentioned above, the analysis program 150 may obtain a plurality of historical medical records 150 from the medical record data structure(s) 146, and may generate time-series data from the medical records 150, as discussed additionally below. The time-series data may represent the medical records 150 as a plurality of respective image blocks that may be stored in the training data data structure 132. When generating the image blocks, the analysis program 126 may access a color key data structure 134 to determine the colors or other graphic effects to apply to the image blocks for respective values of respective parameters of the image blocks. The model building program 128 may subsequently use the image blocks as training data to train a machine learning model 130.

The analysis program 126 may receive patient information 152 for the selected patient 114 from one or more of the users 112 who desire to receive a therapy plan for the selected patient 114. For example, suppose one of the users 112, such as the first user 112(1) is the doctor in charge of the patient 114. The user 112 may submit the patient information 152 for the selected patient 114 to the analysis program 126. In response, the analysis program 126 may generate one or more image blocks (or matrices) from the patient information 152 and use these as input into the machine learning model 130. The machine learning model 130 may output one or more therapy plans (e.g., along with a probability of a predicted improvement in the patient's FIM score (or other quantified disability status) for each therapy plan) and may provide this to the analysis program 126.

One example of a technique that may be used for quantifying the disability status of a patient is the FIM scoring system. The FIM scoring system is an assessment tool that can be used to quantify the functional status of patients throughout a rehabilitation process, such as following a stroke, traumatic brain injury, spinal cord injury, or debilitating cancer. FIM scores may be interpreted to indicate a level of independence of the patient and/or a level of burden of care for a caregiver. The FIM scale may be used to assess how well a person can carry out basic activities of daily living and how heavily dependent the person will be on help from others.

As an example, the FIM may be comprised of 18 items grouped into two subscales, namely, the motor subscale and the cognition subscale. The motor subscale includes: eating, grooming, bathing, dressing upper body, dressing lower body, toileting, bladder management, bowel management, bed/chair/wheelchair transfers, toilet transfers, bath/shower transfers, walk/wheelchair, and stairs. Further, the cognition subscale includes: comprehension, expression, social interaction, problem solving, and memory. Each item may be scored on a seven-point ordinal scale, ranging from a score of 1 to a score of 7. The higher the score, the more independent the patient is in performing the task associated with that item. A guide for scoring may be as follows: (1)—total assistance with helper; (2)—maximal assistance with helper; (3)—moderate assistance with helper; (4)—minimal assistance with helper; (5)—supervision or setup with helper; (6)—modified independence with no helper; and (7)—complete independence with no helper.

The total score for the FIM motor subscale (the sum of the 13 individual motor subscale items) will be a value between 13 and 91 points. The total score for the FIM cognition subscale (the sum of the 5 individual cognition subscale items) will be a value between 5 and 35 points. The total FIM score (i.e., the sum of the motor and cognition subscale scores) may be a value between 18 and 126 points. Furthermore, while the FIM score is used as one example of expressing a quantified disability status of a patient, other techniques or systems for expressing the quantified disability status of the patient may be used herein, as will be apparent to those of skill in the art having the benefit of the disclosure herein.

The analysis program 126 may send the therapies and estimated FIM gain 160 to the requesting user 112(1). In addition, the therapies and estimated FIM gain 160 may also be sent to the other users 112(2) and 112(3) who may provide the therapy to the patient 114. In some cases, the first user 112(1) may instruct the analysis program 126 to send the therapies and estimated FIM gain 160 directly to the other users 112(2) and 112(3), while in other examples, the first user 112(1) may perform forwarding of the therapies and estimated FIM gain 160 to the other users 112(2) and 112(3).

As one example, suppose that the second user 112(2) is a physical therapist and that the third user 112(3) is an occupational therapist. The users 112(1), 112(2), and 112(3) may use the GUI provided by the client program to coordinate the therapies selected determined by the machine learning model 130 to apply the therapies to the patient 114 based on the plan provided by the analysis program 126.

In addition, in other examples, the analysis program 126 may send therapy control information 162 directly to the therapy device 110 to control the therapy device 110 based on the selected therapy plan specified by the machine learning model 130. For instance, suppose that the therapy device 110 is a locomotion therapy device and that the selected therapy specifies that the locomotion therapy should be applied to move the legs of the patient for a period of 45 minutes per day, every other day. The therapy control information 162 may automatically program the therapy device 110 to apply the therapy to the patient 114 as specified by the therapy plan received from the machine learning model 130. Accordingly, implementations herein are able to improve the operation of the therapy device 110 by providing control information that optimizes the treatment provided by the therapy device 110. Furthermore, while several example applications are discussed with respect to FIG. 1, numerous other variations will be apparent to those of skill in the art having the benefit of the disclosure herein.

Figure 2:
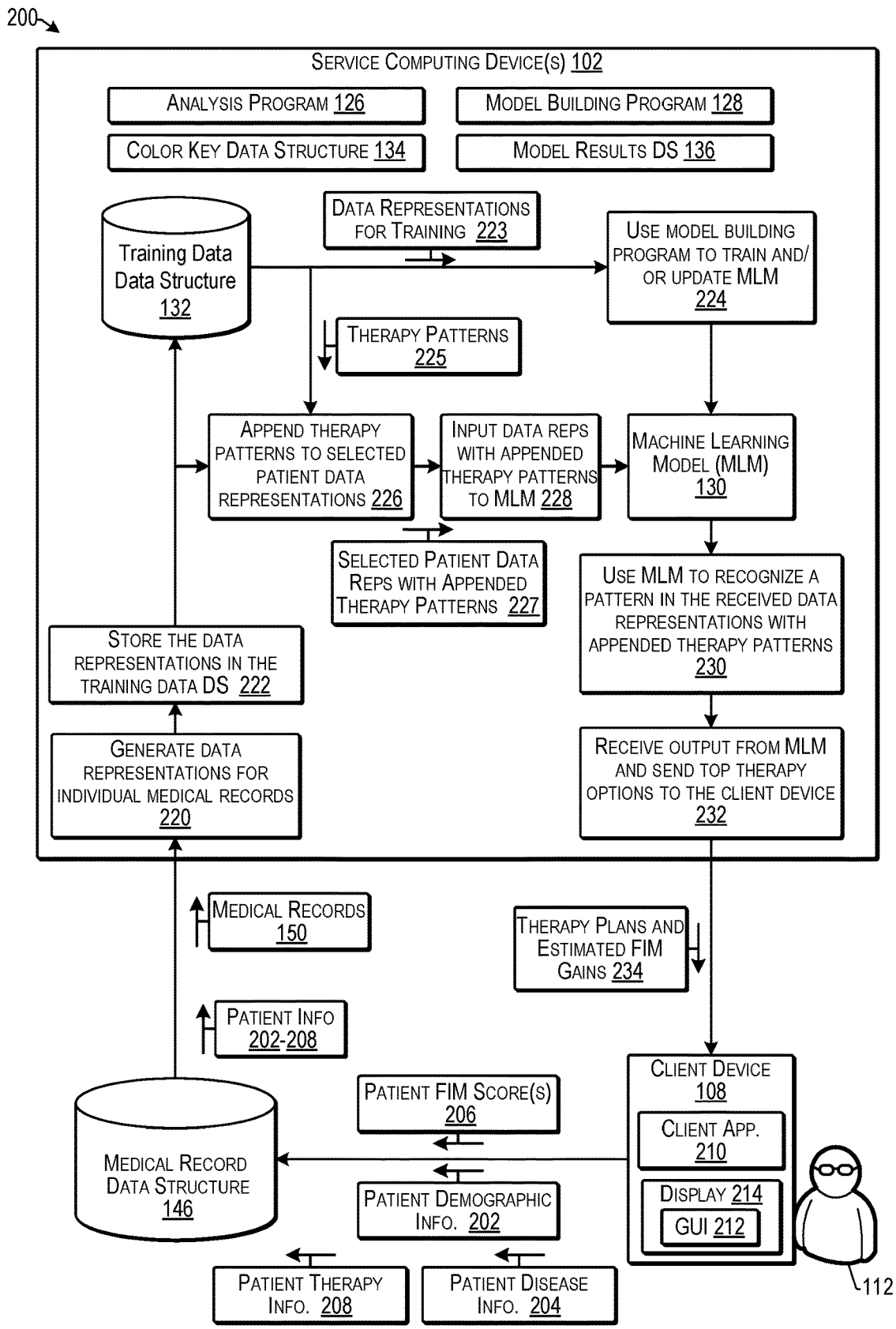
FIG. 2 illustrates an example processing flow for generating a therapy plan according to some implementations.
Figure 7:
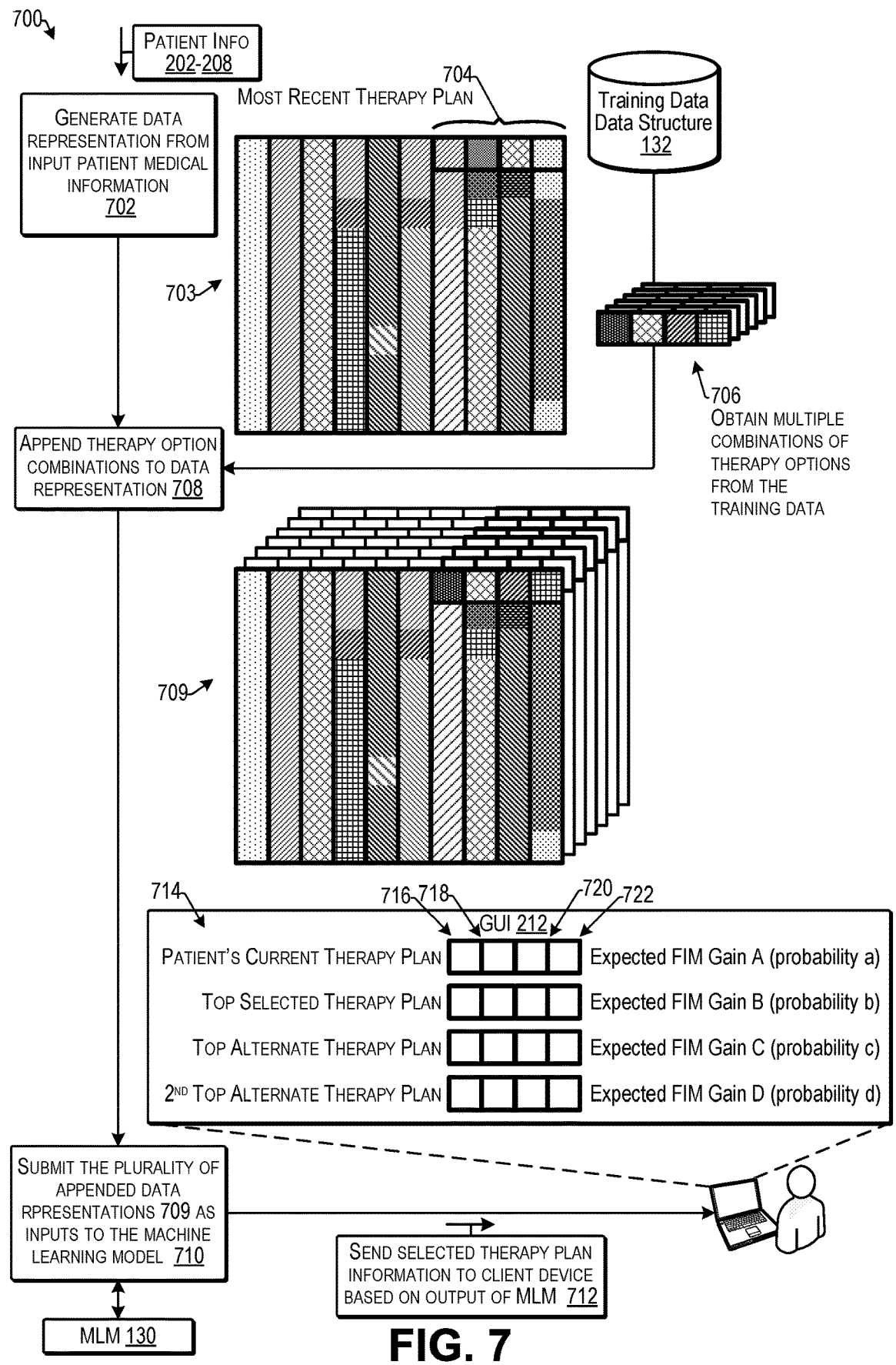
FIG. 7 illustrates an example process for determining one or more therapy plans using patient information as input according to some implementations.
Figure 11:
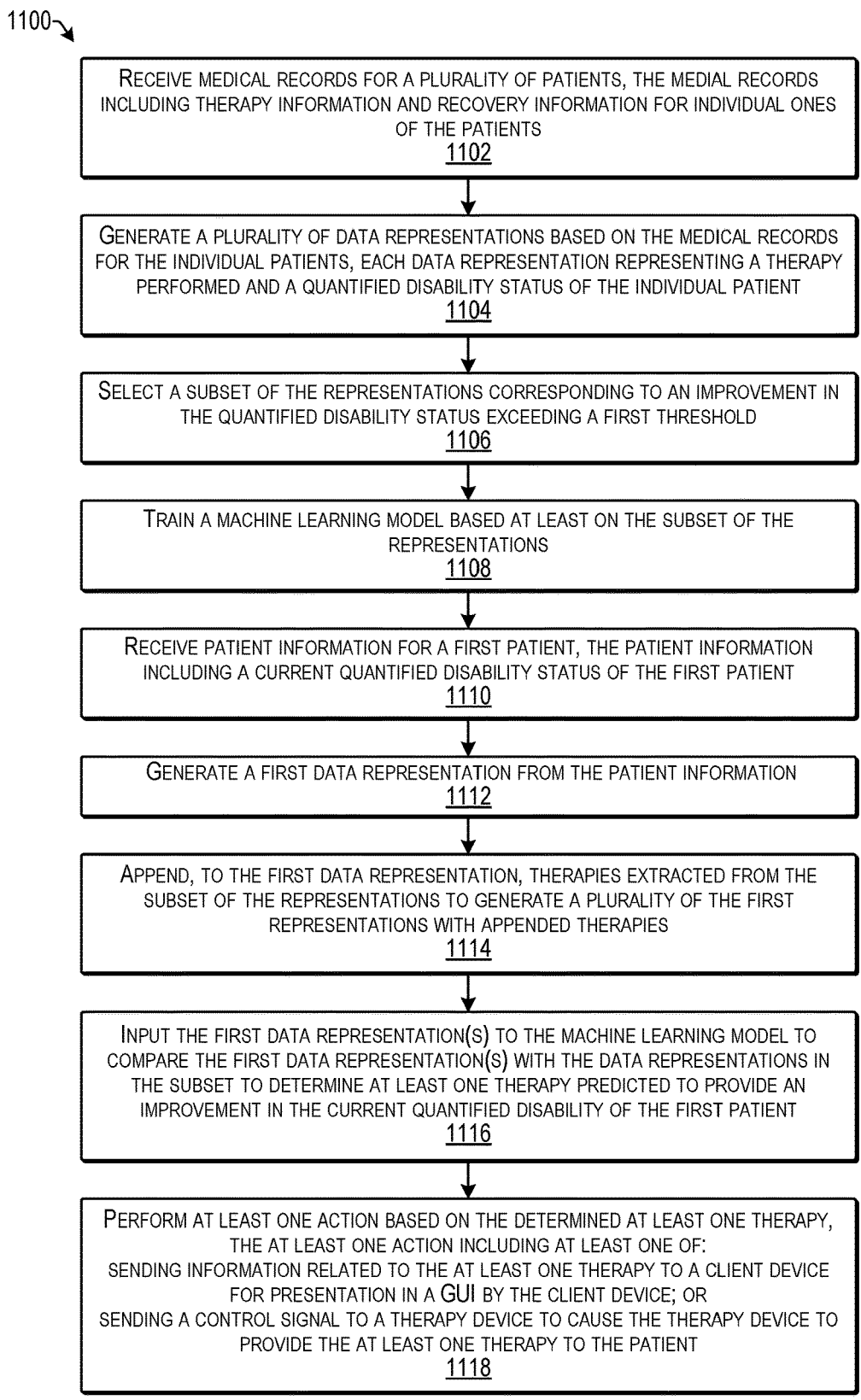
FIG. 11 is a flow diagram illustrating an example process for using machine learning to determine a therapy plan according to some implementations.

FIGS. 2, 7, and 11 include flow diagrams illustrating example processes according to some implementations. The processes are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the processes are described with reference to the environments, frameworks, and systems described in the examples herein, although the processes may be implemented in a wide variety of other environments, frameworks, and systems.

FIG. 2 illustrates an example processing flow 200 for generating a therapy plan according to some implementations. The process may be executed at least partially by the analysis program 126 executing on the service computing device 102 or other suitable computing device.

In this example, the user 112 may use the client device 108 to submit information about a selected patient to the analysis program 126, either directly, or via the medical record data structure 146, from whence the analysis program 126 may access the patient information. As one example, suppose that the user 112 submits patient demographic information 202, patient disease information 204, patient FIM score(s) 206, and patient therapy information 208, such as therapies that the patient may have undergone in the past, to the medical record data structure 146. For instance, a client application 210 executing on the client device 108 may present a GUI 212 on a display 214 of the client device 108. The user 112 may manipulate the GUI 212 to provide the patient information 202-208 to the medical record data structure 146, and for invoking the analysis program 126 to determine a therapy plan for the selected patient based on the patient information 202-208. The medical records of other patients contained in the medical record data structure 146 may include similar information.

In some examples, the client application 210 may be a browser that accesses the medical record data structure 146 and/or the analysis program 126 through a web-based platform. In other examples, the client application 210 may be dedicated and/or proprietary application for accessing the medical record data structure 146 and/or the analysis program 126.

To obtain time-series data for use as training data for generating the machine learning model 130, the analysis program may obtain medical records 150 for a plurality of past patients from the medical record data structure 146. Each obtained medical record 150 may include some or all of the patient information discussed above, such as patient demographic information 202, patient disease information 204, patient FIM scores 206, and patient therapy information 208.

At 220, the analysis program 126 may generate a data representation from each of the medical records 150 corresponding to an individual patient. The analysis program 126 may generate each data representation representing a patient medical record 150 in the format of a matrix or an image using the historical patient demographic, disease, therapy, and recovery information stored in the electric medical record database 146. Furthermore, when generating the time series blocks as images, the analysis program 126 may use the information in the color key data structure 134 when constructing each data representation as an image, as discussed additionally below, e.g., with respect to FIG. 5.

At 222, the analysis program 126 may store the generated data representations in the training data data structure 132 as training data.

At 224, the analysis program 126 may invoke the model building program 128 to train and/or update the machine learning model 130. The model building program may obtain a plurality of data representations 223 for training the machine learning model 130 from the training data data structure.

At 226, the analysis program 126 may receive the patient information 202-208 for the selected patient, generate a selected patient data representation as indicated at 220, store the selected patient data representation in the training data data structure, as indicated at 222, and append multiple therapy patterns 225 obtained from the training data data structure 132 to generate a plurality of selected patient data representations 227 with different therapy patterns. For example, the therapy patterns selected for appending to the patient data representation may be those determined to result in a threshold FIM gain or other gain in disability status improvement. Appending respective therapy patterns to the patient data representation results in a plurality of the patient data representations, each having a different therapy plan appended thereto.

At 228, the analysis program 126 may input the patient data representations with the appended therapy patterns to the machine learning model 130.

At 230, the analysis program 126 may use the machine learning model to recognize a pattern in the received selected patient data representations. For example, the machine learning model may determine one or more of the data representations of the training data that match one or more of the patient data representations having appended therapy patterns within a threshold probability.

At 232, the analysis program 126 may receive the output from the machine learning model 130, and may send the top therapy options to the client device 108. For instance, as discussed below, the top therapy options may be those determined by the machine learning model to have the highest probability of a match with data representation having a gain in the FIM score.

Accordingly, as indicated at 234, the top therapy plans and the estimated FIM gains 234 may be sent to the client device 108. The client application 210 on the client device may receive the therapy plans and estimated FIM gains 234, and may present them in the GUI 212 on the display 214. The user 112 may view the therapy plans determined by the machine learning model. In some examples, the user 112 may select one of the therapy plans to apply to the selected patient, such as the therapy plan corresponding to the highest probability. In some cases, there may be multiple therapy options with similar probabilities, in which case the therapy plan that maximizes the expected gain of the FIM score, and these multiple therapy options may be visualized on the GUI 212. Thus, according to the techniques described above, it is possible to visualize the performance of recovery expected from a therapy plan and multiple therapy options, which may enable maximizing of the expected recovery based on the result of the MLM recognition of the time-series data related to historical therapy and recovery records for individual patients by analyzing medical data in a medical record data structure.

Figure 3:
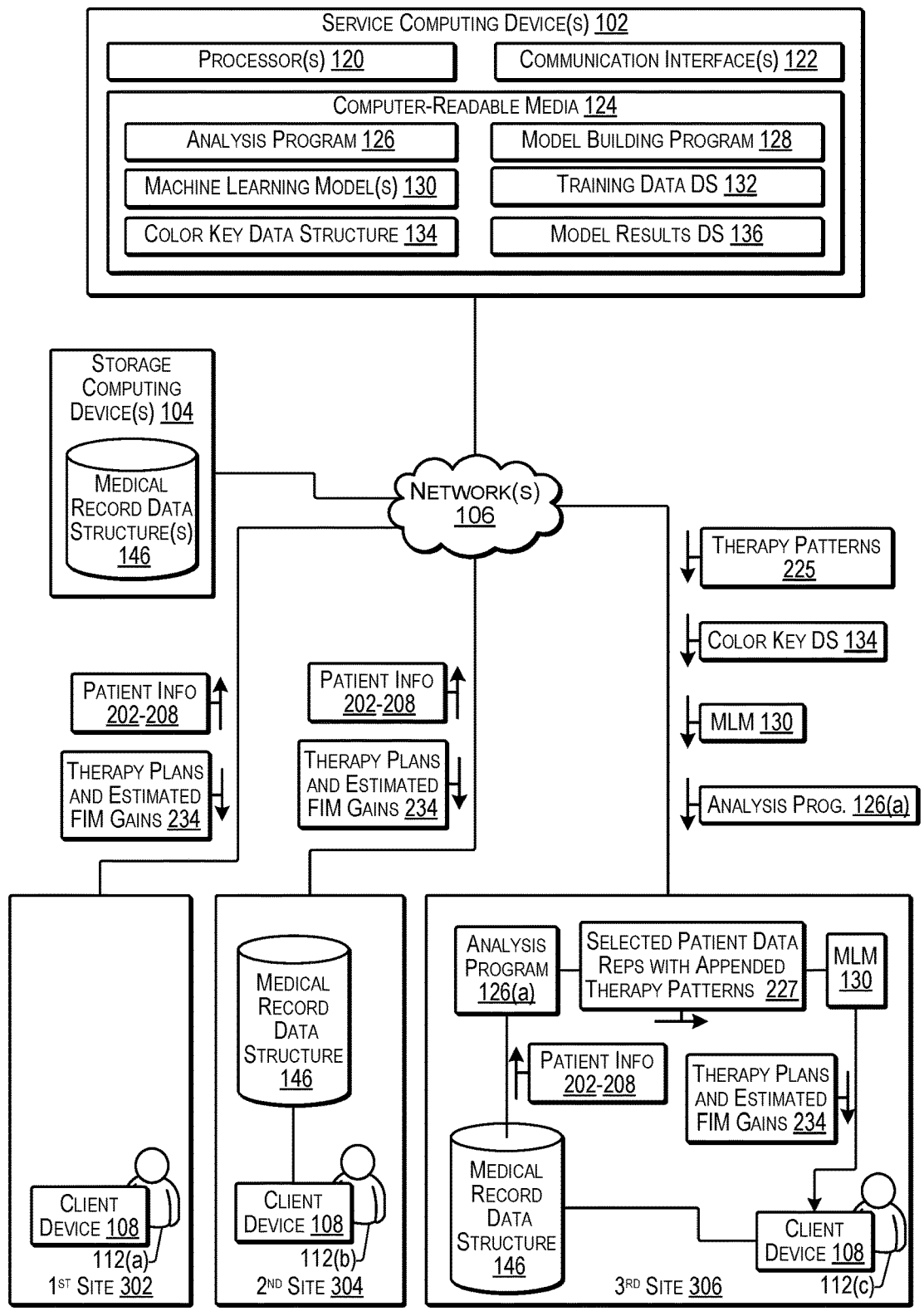
FIG. 3 illustrates example site hardware and software configurations for various sites according to some implementations.

FIG. 3 illustrates example site hardware and software configurations 300 for various sites according to some implementations. In the illustrated example, three different example site configurations are illustrated including a first site 302, a second site 304, and a third site 306. Each site 302, 304, and 306 may be a hospital, a recovery facility, a research facility, a nursing home, or other facility or location at which a medical professional or other user 112 may be managing patient therapies. The example of the first site 302 may include a hardware and software configurations similar to that discussed above with respect to FIG. 2 in which the client device 108 accesses the storage computing device 104 and the service computing device 102 remotely over the one or more networks 106. Accordingly, this configuration has the advantage of using the service for providing therapy plans and estimated FIM gain 234 without the user having to maintain the medical record storage data structure 146 or other hardware or software, and therefore may be provided at a lower cost to the user 112(*a*). On the other hand, in this case, the patient information 202-208 is sent over the one or more networks 106 and is stored remotely. Accordingly, the configuration of the first site 302 may be less secure.

The example of the second site 304 includes the medical record data structure 146 stored locally at the second site 304. Consequently, in this example the patient information 202-208 is still required to be sent over the one or more networks 106 to the service computing device 102, but not to the storage computing device 104. Consequently, the configuration of the second site 304 may be more secure than that of the first site 302. For example, the patient information 202-208 may be encrypted, anonymized, or otherwise protected prior to being sent to the service computing device 102, and thus, no patient identifying information might be stored off site. The example of the second site 304 may include increased cost over the example of the first site 302 in that the user 112(*b*) maintains the medical record data structure 146 locally on site.

The example of the third site 306 includes the medical record data structure 146 stored locally at the third site 306, as well as including a version of the analysis program 126(*a*) maintained and executed locally. For example, the user 112(*c*) may download or otherwise obtain a full version or an abridged version of the analysis program 126(*a*), which may include functionality for converting the patient information 202-208 into data representations locally and appending therapy patterns 225 to the locally generated data representations 227. In addition, the user 112(*c*) may download the machine learning model 130 and the color key data structure 134. For example, the color key data structure 134 may be used by the analysis program 126(a) when generating the data representations as images rather than matrices. In addition, the machine learning model 130 may determine one or more therapy plans and estimated FIM gains 234, and provide these to the client application on the client device 108.

Accordingly, the example third site 306 may be able to maintain the patient information more securely than the first site 302 or the second site 304. Furthermore, the user 112(c) may regularly download updated versions of the machine learning model 130 and/or the analysis program 126(a). However, the configuration of the third site 306 may require additional computing devices for executing the analysis program 126(a) and the machine learning model 130, as well as for maintaining the medical record data structure 146 locally.

Figure 4:
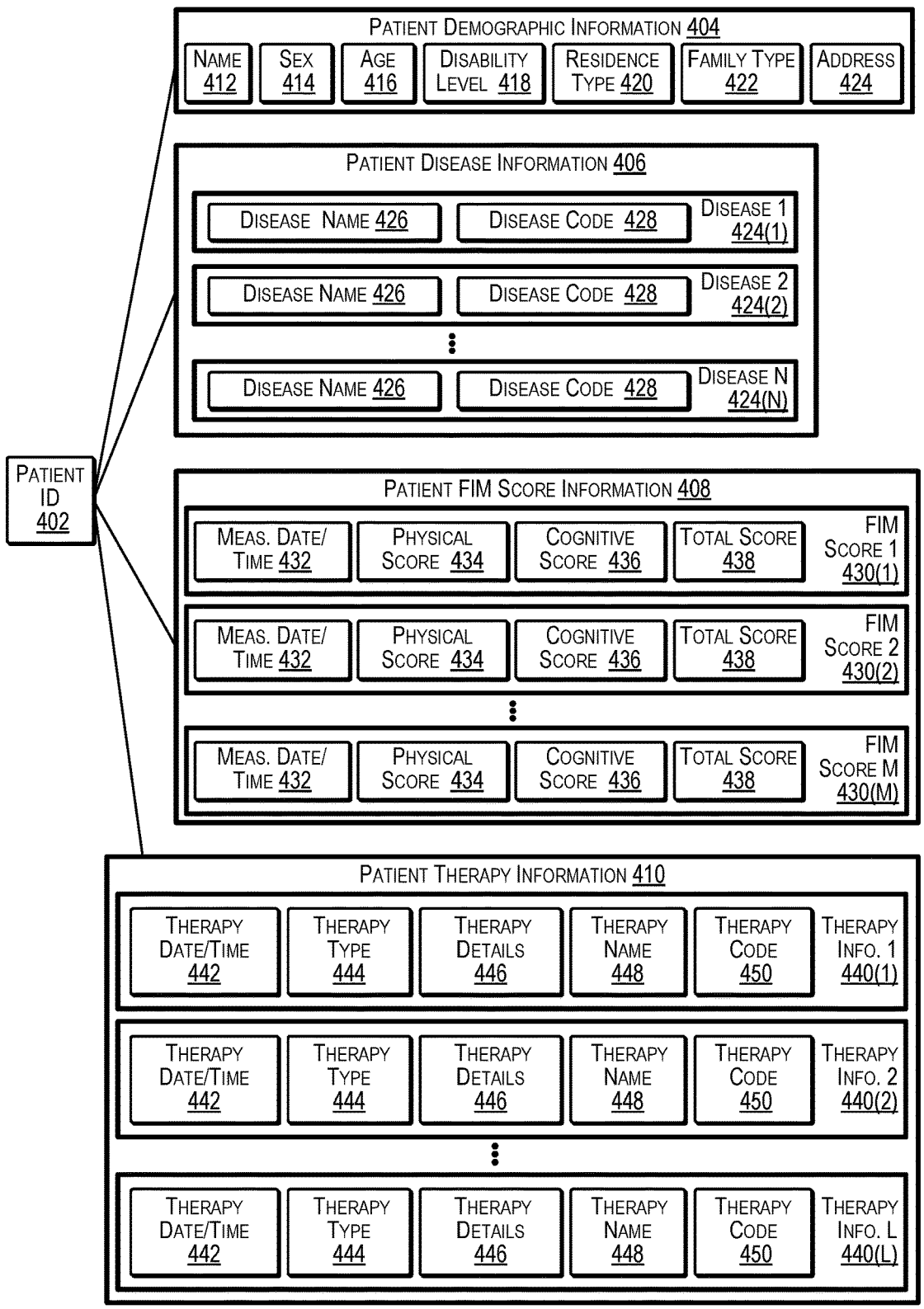
FIG. 4 illustrates an example format for storing the patient information in a medical record database according to some implementations.

FIG. 4 illustrates an example format for storing the patient information 400 in a medical record database according to some implementations. In this example, the patient information 400 includes a patient identifier (ID) 402 which may be a patient ID number, patient account number, or the like, by which the patient may be uniquely identified or otherwise individually distinguished in the medical record data structure. The patient information 400 further includes patient demographic information 404, patient disease information 406, patient FIM score information 408, and patient therapy information 410. Accordingly, the patient ID 402 is associated with each of the types of patient information 404-410. In some examples, the patient demographic information 404 and the patient disease information 406 may be considered fixed information while the patient FIM score information 408 and the patient therapy information 410 may be considered historical information.

The patient demographic information 404 may include a patient name 412, sex 414, age 416, disability level 418, residents type 420, family type 422, and address 424. In addition, the patient disease information 406 may include a listing of diseases such as a first disease 424(1), a second disease 424(2), through an Nth disease 424(N). For each disease listed, the disease information 406 may include a respective disease or disability name 426 and a corresponding disease code 428. For example, each disease code 428 may be correlated to a particular color or other graphic effect in the color key database 134 as discussed additionally below, and may be used for representing the disease in the data representations.

The patient FIM score information 408 may include one or FIM scores determined for the particular patient, such as a first FIM score 430(1), a second FIM score 430(2), through an Mth FIM score 430(M). Each FIM score may include information and metadata such as the measurement date and time 432 the physical score 434, the cognitive score 436, and the total score 438. In addition, in some cases, in addition to having the total physical score 434 and the total cognitive score 436, the FIM score information 408 may include the score for each of the sub categories of the physical score and the cognitive score.

The patient therapy information 410 may include therapy information for a plurality of therapies that have been implemented by the patient in the past, such as first therapy information 440(1), seconded therapy information 440(2), through Lth therapy information 440(L). Each therapy information 440 may include a therapy date and time 442, a therapy type 444, therapy details 446, the therapy name 448, and a therapy code 450. Each therapy code 450 may be correlated to a particular color or other graphic effect in the color key data structure 134 as discussed additionally below.

Figure 5:
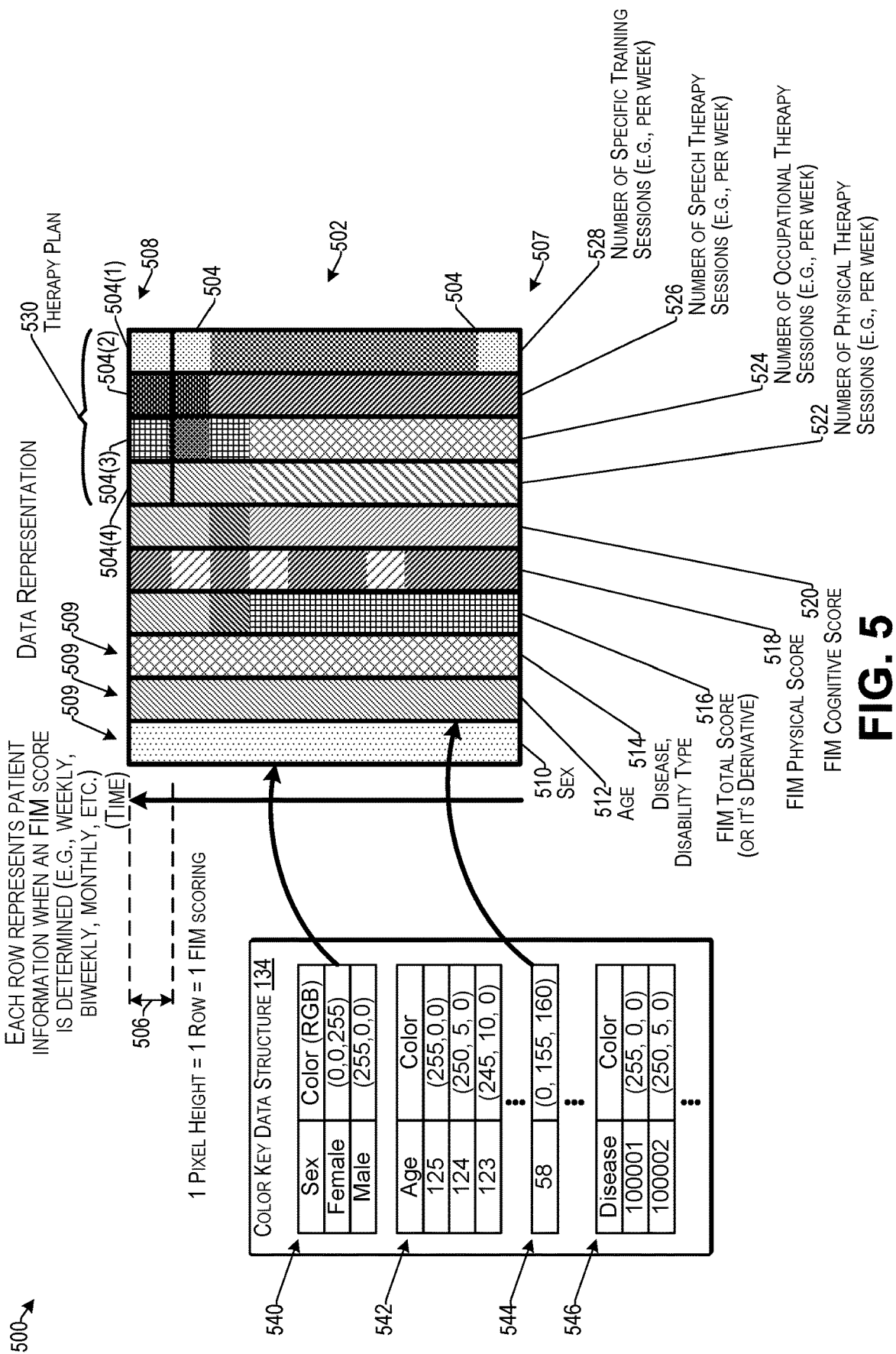
FIG. 5 illustrates an example data representation representing an input patient medical record summarized as an image according to some implementations.

FIG. 5 illustrates an example data representation 500 representing an input patient medical record summarized as an image according to some implementations. In some examples, the data representation 500 is a data representation generated by the analysis program 126 (not shown in FIG. 5) using a patient medical record received from the medical record data structure and/or the client computing device, e.g., as discussed above with respect to FIGS. 1-3. For example, the analysis program may create a data representation 500 using the patient information, e.g., as set forth in FIG. 4. In this example, the generated data representation 500 is an image 502 with multiple colored blocks (also referred to as pixels) 504 arranged in height and width. In other examples, as discussed additionally below with respect to FIG. 10, the data representations may be represented as a matrix with multiple dimensions.

In the illustrated example, the analysis program generates the data representation 500 from a received medical record as an image 502 composed of the multiple blocks 504. As discussed additionally below, each block 504 may have a color or other graphic effect applied to it that corresponds to a value of the patient data. The data representation 500 is divided in the vertical direction into a plurality of time-based intervals or rows 506 corresponding to one block 504 each in which the vertical interval of one block 504 represents a corresponding time cycle. As one example, each row 506 may correspond to the state of the patient information when a new FIM scoring is performed. For example, the FIM score (or other quantified disability status) of a patient may be determined on a periodic basis such as every few days, weekly, biweekly, monthly, and/or at varying time intervals. Alternatively, in other examples, the rows 506 may be based on a consistent regular time period such that each row corresponds to one day, one week, one biweek, one month, etc., regardless of whether a new FIM score has been determined.

The actual size and resolution of the blocks 504 and/or the corresponding data representation 500 may be controlled based on a tradeoff between a desired resolution and a desired storage efficiency, i.e., the higher the resolution of the data representation 500, the more storage consumed by the training data data structure, and the more memory required when training the machine learning model, but the higher the resolution, the higher the accuracy during comparison of data representations. Further, the data representations 500 may all be generally the same size and/or may be scalable to be the same size to enable comparison or matching with others of the data representations 500. Accordingly, in this example, the data representation 500 is an image 502 that represents a summary of some information in the received medical record of a patient. The image 502 may be used during the machine learning recognition process described above with respect to FIGS. 1-3, thus enabling the use of pattern recognition machine learning for determining one or more optimal therapy plans for a patient.

In addition, the height, i.e., the number of rows 506 in the data representations 500 may be specified by a user or may be specified by default. For example, when more data is included in each column 509 in the data representations 500, there may be fewer overall data representations 500 to use as training data. On the other hand, shorter data representations 500 may be more subject to random variations, and therefore may not produce as accurate results.

In some examples, each time a new row is added to the top of a data representation 500, a row may be removed from the bottom of the data representation 500 to thereby generate a new data representation 500 that may be added to the training data and/or analyzed using the machine learning model. In some examples, the old block may be retained in the training data data structure, while in other examples, the old block may be deleted from the training data data structure. Thus, in FIG. 5, the data representation 500 has older data toward the bottom 507 of the data representation 500 and newer data toward the top 508 of the data representation 500. This order may be reversed in other examples, or, as another example, the patient information may be represented chronologically in a horizontal direction rather than vertically.

The data representation 500 includes multiple vertical pixel bands referred to as columns 509 each of which corresponds to a patient information parameter that may have one or more data values associated therewith. In this example, patient information parameters represented by the columns 509 include patient sex 510, age 512, disease or disability type 514, FIM total score 516, FIM physical score 518, FIM cognitive score 520, number of physical therapy sessions per time interval 522, number of occupational therapy sessions per time interval 524, number of speech therapy sessions per time interval 526, and number of specific training sessions per time interval 528. In some cases, a derivative of the FIM total score 516 may be used instead of FIM total score 516. The value of disease or disability type 514 is categorized and determined by the code of the disease or disability type, e.g., as mentioned above with respect to FIG. 4. Furthermore, while certain patient information parameters are represented in the example of FIG. 5, in other examples more, fewer, or different patient information parameters may be used for the columns 509.

In addition, the analysis program may assign colors or other graphic effects, such as patterns, cross-hatching, or the like, to specific values or ranges of values for each patient information parameter 510-528. As one example, the color key data structure 134 may be used by the analysis program for determining the color or other graphic effect to use for a particular value or range of values for a particular parameter. For instance, as a simple example, suppose that an RGB color model is used, with each color (Red, Green, and Blue) having a possible value assigned between 0 and 255. Thus, for each parameter (column) (e.g., age, disease, FIM score, etc.), there are $256^3$ possible gradations of color values that may be assigned. In addition, one block of a full-color image data may typically have 8 bits of data for each color of red, green, and blue, for a total of 24 bits of color data. Additionally, one block of gray-scale image data may typically have 8 bits of data representing brightness. Accordingly, in some examples, herein it may be practical to limit the number of colors to, e.g., 256 colors, which would reduce the amount of storage required for the colors (e.g., 8 bits per color, rather than 24 or more bits) while still enabling a gradation of 256 different values or ranges of values for each patient information parameter, which may be sufficient for most or all parameters.

As one example, the color key data structure may include color assignments for each possible value for each patient information parameter 510-528. For instance, as indicated at 540, for patient sex there are two possible parameter values, i.e., female, which has the color blue (0,0,255) assigned, and male, which has the color red (255,0,0) assigned. In this example, supposed that the patient is a female, so the blocks in the first column corresponding to the patient sex 510 are all colored blue, i.e., RGB value (0,0,255). In addition, as indicated at 542, different colors may be assigned to different ages such as on a per-year basis, e.g., from age 0 through 125. Thus, as indicated at 544, suppose that the patient is 58 years old. Accordingly, a color corresponding to age 58 in the color key data structure 134 may be applied to the blocks in the column for patient age 512. As indicated at 546, colors or other graphic effects may similarly be assigned to different disease codes, and other values of the other parameters 514-528.

Further, while the RGB color model is described herein as one example of a color model that may be used with some implementations herein, numerous other additive color models, subtractive color models, or other color models or variations of color models may be used in the examples herein. Accordingly, implementations herein are not limited to any particular color model for representing and/or producing the colors. In addition, other graphic effects such as patterns, crosshatching, varying degrees of brightness, or the like, may be used in addition to or in place of colors in some examples herein.

In the illustrated example, four blocks 504(1), 504(2), 504(3), and 504(4) on the top row of columns 522-528 may represent a therapy plan 530. In the case of a new patient, the blocks 504(1)-504(4) may become one therapy plan, and the combination of occupational therapy, speech therapy, physical therapy, and/or specific training represents the therapy plan 530. As discussed above, e.g., with respect to FIGS. 2 and 3, the analysis program may append different therapy plans to the data representation 500 at blocks 504(1) through 504(4), and may attempt to find similar data representations 500 with the different therapy plans using the machine learning model. The analysis program may use the appended data representations 500 as inputs to the machine learning model to recognize similar patterns in the data representation 500 for locating similar data representations with therapy plans that produce good recovery results (e.g., a highest gain in the FIM score(s)). As mentioned above, as one example, the machine learning model herein may be based on a deep learning algorithm such as CNN (Convolutional Neural Network), although other types of machine learning models may alternatively be used, as enumerated above.

The machine learning model may provide as an output, the top matching configuration of data representations, e.g., with a probability of match, and with a predicted gain in the FIM score. The analysis program may select the highest FIM gain corresponding to the highest probability of a match and determine the therapy plan 530 corresponding to the four blocks 504(1)-504(4). In some cases, the analysis program may provide the top three, top five, etc., therapy plans along with the predicted FIM gains for each and, in some cases, the probability of the match. Furthermore, analysis program may send this information to the client device for presentation to the user in the GUI.

Figure 6:
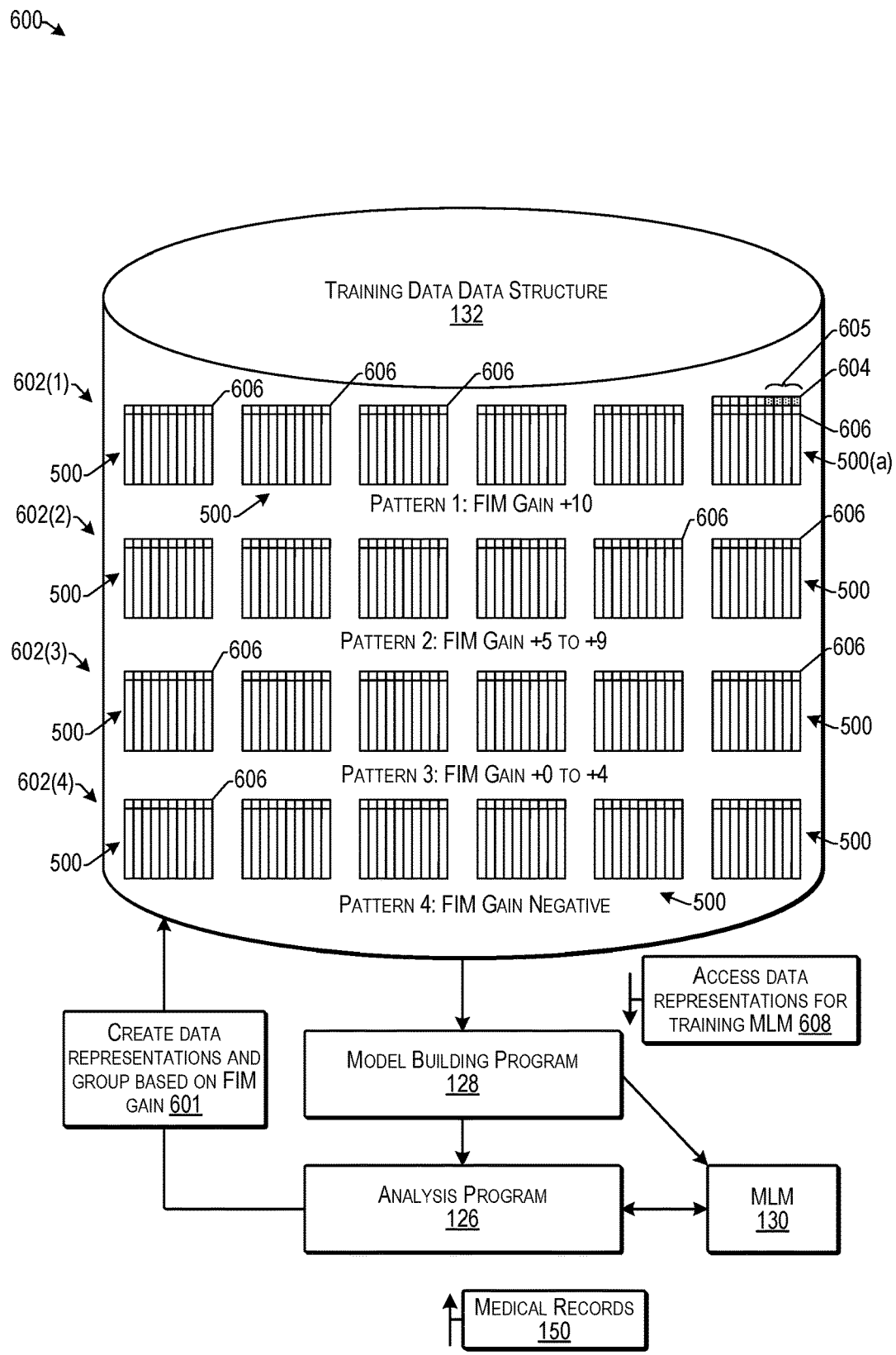
FIG. 6 illustrates an example of generating a machine learning model using the data representations for training the machine learning model according to some implementations.

FIG. 6 illustrates an example 600 of generating the machine learning model using the data representations 500 for training the machine learning model according to some implementations. In this example, the analysis program 126 receives the medical records 150, and, as indicated at 601, the analysis program 126 creates a plurality of data representations 500 from the received medical records 150, and classifies or otherwise groups the data representations 500 into subsets 602 based on FIM gain (or other gain in a quantified disability status). For example, the training data data structure 132 may include a plurality of the data representations 500 generated by the analysis program 126 as discussed above with respect to FIGS. 1, 2, and 5.

In this example, the analysis program 126 organizes the plurality of data representations 500 into a plurality of subsets 602(1), 602(2), 602(3), and 602(4) based on threshold ranges for a determined amount of FIM gain. As mentioned above, FIM gain is the difference between a previous FIM score and a current FIM score (i.e., the total FIM score corresponding to parameter 516 in the data representation 500 of FIG. 5 or a derivative of the total score). The analysis program 126 may group the data representations 500 into the subsets 602(1)-602(4) by calculating the FIM gain of the most recently measured FIM score using the difference determined between the upper two rows 604 and 606 of each data representation 500 in which the upper row 604 includes the most recent data and row 606 includes the data immediately preceding the data in row 606. In this example, the data representations 500 with FIM gains of 10 points or more are classified as "Pattern 1" and grouped into subset 602(1). The data representations 500 with FIM gains of 5-9 points are classified as "Pattern 2" and grouped into subset 602(2). The data representations 500 with FIM gains from 0-4 points are classified as "Pattern 3" and grouped into subset 602(3). The data representations 500 with minus FIM gains are classified as "Pattern 4" and are grouped into subset 602(4).

Following the determination of the FIM gain for an individual data representation 500, the analysis program 126 may delete the upper row 604 from each data representation 500, so that when matching is performed, the data representations 500 with the deleted upper row are used. The upper row 604 corresponds to the most recent patient input data. Following deletion of the upper row 604, row 606 is the upper row. Before deleting the upper row 604 for each data representation 500, the analysis program may save the therapy plan blocks 605 (i.e., corresponding to blocks 504(1)-504(4) in FIG. 5) from the upper row 604 of each data representation 500 in at least the first subset 602(1) (Pattern 1) for use in appending therapy plans to patient data representations as discussed below with respect to FIG. 7). In the illustrated example, the data representations 500 have each had the upper row deleted except for data representation 500(*a*), which shows the upper row 604 before deletion for discussion purposes.

Following deletion of the upper row 604 from each data representation 500 in the training data data structure 132, the model building program 206 may be invoked to access the data representations 500 in the training data data structure 132, as indicated at 608, for generating the machine learning model 130. The machine learning model 130 may be trained using at least the grouped (classified) data representations 500 in the first subset 602(1) (Pattern 1), for generating the trained machine learning model 130. In some examples, the machine learning model 130 may be a classifier that uses a deep learning algorithm or other algorithm, such an algorithm that performs categorization based on the distance between matrixes. As one example, in a non-deep learning algorithm, the pattern may be determined by the ratio of each pattern of training data included within a constant distance from original patient's data. For instance, if the ratio of Pattern 1 is large, the machine learning model 130 recognizes that case as corresponding to subset 602(1) with an expected FIM gain of 10 points or more (i.e., Pattern 1).

FIG. 7 illustrates an example process 700 for determining one or more therapy plans using patient information as input according to some implementations. The example process 700 may be executed by the analysis program 126 running on the service computing device 102 or other suitable computing device.

At 702, the analysis program receives the patient information 202-208 for a selected patient as discussed above, e.g., with respect to FIG. 2, and generates a data representation 703 using the techniques discussed above with respect to FIG. 5. For instance, the data representation 703 may include the most recent therapy plan as indicated at 704.

At 706, the analysis program may obtain multiple combinations of therapy options from the training data. In particular, the multiple combinations of therapy options may be extracted from the data representations in subset 602(1) (Pattern 1) discussed above with respect to FIG. 6 (e.g., at 605). The data representations in subset 602(1) correspond to the highest FIM gains stored in the training data structure 132. In some examples, the data representations from which the multiple therapy options are extracted are selected in an ascending order of the difference from the data representation 703. For instance, the difference may be calculated by the distance between matrixes.

At 708, the analysis program may append the multiple combinations of therapy options to the data representation 703 to create a plurality of data representations 709. In other words, the analysis program substitutes the therapy options extracted from subset 602(1) as discussed above with respect to FIG. 6 in place of the most recent therapy plan 704 on the patient data representation 703 to generates a plurality of new data representations 709, each having one of the different therapy plans extracted from the highest FIM gain subset 602(1) in the training data data structure 132. In addition, the original therapy plan of the patient may also be included in the plurality of data representations 709.

At 710, the plurality of data representations 709 is used as inputs to the machine learning model 130. The machine learning model 130 may perform classification on the plurality of data representations 709 by recognizing patterns using the data representations for classification prepared for each patient. In some examples, the machine learning model 130 may use a deep learning algorithm or an algorithm based on the distance between matrixes. As an example, in a non-deep learning algorithm, the pattern may be determined by the ratio of pattern of training data included within a constant distance from original patient's data. The pattern (corresponding subset) may be determined by comparing the ratio of each pattern with that of the training data. If the ratio of Pattern 1 is large or larger than that of the training data, the machine learning model 130 recognizes that case as corresponding to the first subset 602(1) (Pattern 1). The machine learning model 130 may indicate which of the data representations 709 most closely match with data representations in the training data.

At 712, the analysis program may receive the output of the machine learning model 130 and may determine the top candidates from the output. For instance, the top candidates may be those appended data representations 709 that are recognized as Pattern 1 and having the highest probability of a match with one or more data representations of the first subset 601(1) (Pattern 1) in the training data 132. If there is no appended data representation 709 that is recognized as corresponding to the first subset 602(1) (Pattern 1), the top candidates may be the appended data representations that are recognized as corresponding to the second subset 602(2) (Pattern 2) or the third subset 602(3) (Pattern 3) and have the highest probability of a match with one or more data representations of the second subset 602(2) (Pattern 2) or the third subset 602(3) (Pattern 3) in the training data 132. If there is no appended data representation 709 that is recognized as corresponding to the first, second, or third subsets (Patterns 1, 2 or 3), the top candidates may be the appended data representation that is recognized corresponding to the fourth subset 602(4)(Pattern 4) and have the lowest probability of a match with one or more data representations of the fourth subset 602(4) (Pattern 4) in the training data 132. In the case of a match with one of the first three subsets, the analysis program may select the top three highest probabilities, top five highest probabilities, or the like. Accordingly, the analysis program may send the results to the client device, and the client application on the client device may present the results in the GUI, as indicated at 714.

In this example, the results 714 presented in the GUI 212 may include the patient's original current therapy plan received with the patient information indicating, e.g., a number of physical therapy sessions 716 per time period, a number of occupational therapy sessions 718 per time period, a number of speech therapy sessions 720 per time period, and/or a number of specific training sessions 722 per time period. The results 714 also include a top selected therapy plan with indicated number of physical therapy sessions 716 per time period, number of occupational therapy sessions 718 per time period, number of speech therapy sessions 720 per time period, and/or a number of specific training sessions 722 per time period. In addition, each therapy plan may include an expected FIM gain of the therapy plan along with the probability determined based on the result of pattern recognition performed by the machine learning model 130. Furthermore, in this example, the results 714 show the selected therapy plan such as the therapy plan having the highest expected FIM gain (i.e., FIM Gain B) and the probability b, which may be compared with the expected FIM gain A of the patient's current therapy plan. The results 714 further show the top two alternative therapy options achieving the next highest expected FIM gains with the expected FIM gains C and D, and the probabilities c and d, respectively. Thus, implementations herein enable visualization of the performance of recovery expected from a selected therapy plan and one or more alternative therapy plans that may maximize the expected recovery of the patient (i.e., improvement in disability status). Accordingly, implementations herein may select an optimal therapy plan based on the results of the pattern recognition of the time-series data about historical therapy and recovery records of a plurality of patients by analyzing medical records.

Figure 8:
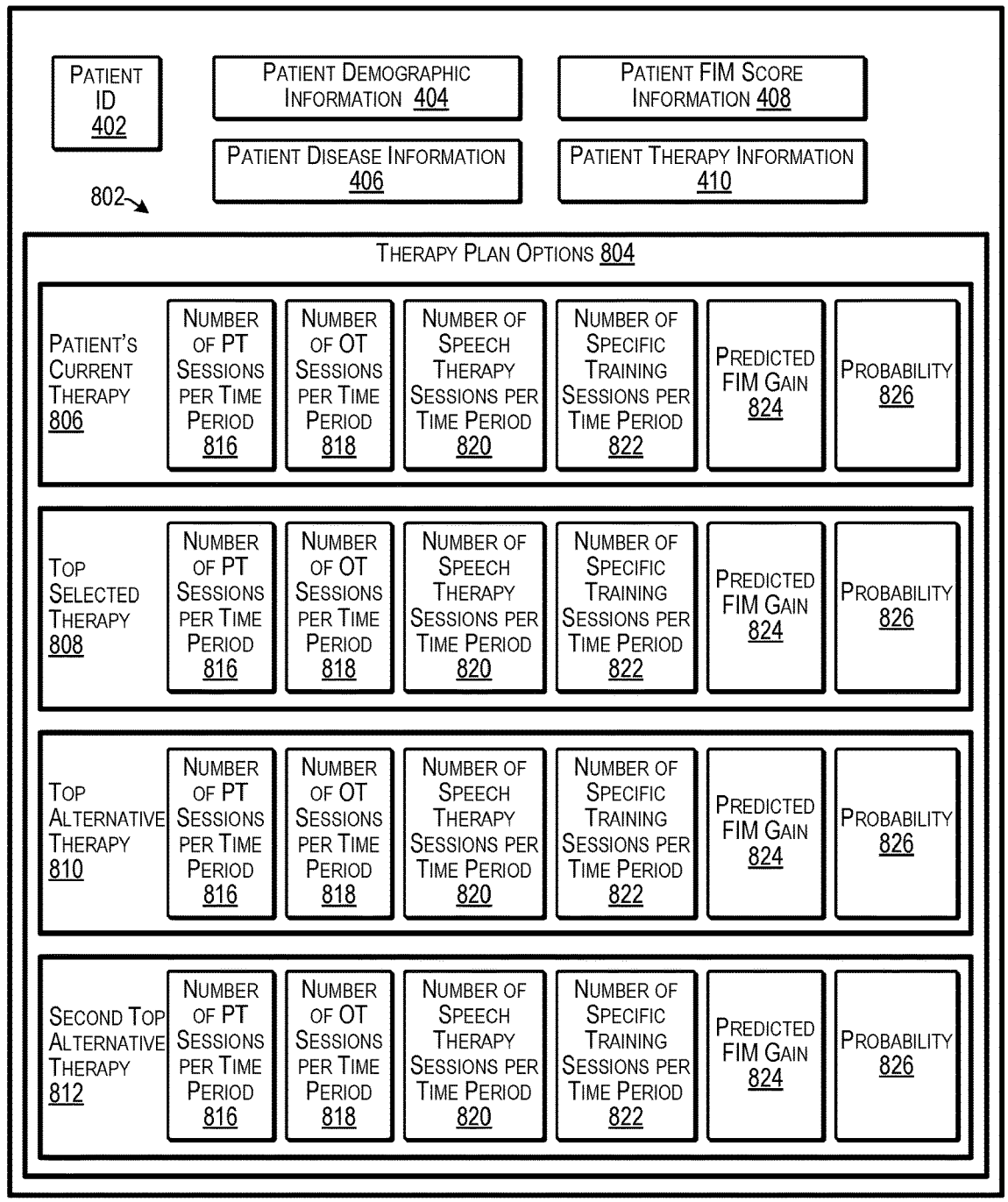
FIG. 8 illustrates an example of a graphic user interface that may be presented by the client application for visualizing the results of the therapy plan analysis according to some implementations.

FIG. 8 illustrates an example of the GUI 212 that may be presented by the client application for visualizing the results of the analysis according to some implementations. In this example, the GUI 212 may present the patient information 400 discussed above with respect to FIG. 4, including the patient demographic information 404, patient disease information 406, patient FIM score information 408, and patient therapy information 410. For example, this information may have been submitted to the analysis application 126 for generating the results 802 of the analysis presented in the GUI 212.

As mentioned above, when the client application (not shown in FIG. 8) receives the results 802 of the analysis from the analysis application, the client application may present the therapy plan options 804 in the GUI 212. In this example, the therapy plan options 804 include the details of the patient's current therapy 806. In addition, the therapy plan options 804 include a top selected therapy 808 determined using the machine learning model, a top alternative therapy 810, and a second top alternative therapy 812. Furthermore, while this example illustrates a selected therapy plan 808 and two alternative therapy plans 810 and 812, in other examples more or fewer alternative therapy plans might be presented. Each of the presented therapy plans may include a number of physical therapy sessions 816 to be performed per time period, a number of occupational therapy sessions 818 to be performed per time period, a number of speech therapy sessions 820 to be performed per time period, a number of specific training sessions 822 to be performed per time period, the predicted FIM gain 824, and the probability 826 indicated by the machine learning model. Thus, according to implementations herein, a medical professional can review the therapy plan options 804 and can combine the best therapy options for improving the performance of recovery for the selected patient.

In addition, as another alternative, the GUI 212 may present case information of other patients having data representations similar to the data representation of the current patient, as indicated at 806. The data representations similar to the current patient's data representation (e.g., block 703 in FIG. 7) may be extracted in an ascending order of the difference from the training data data structure, e.g., based on the Euclid distance between matrixes. Thus, the predicted FIM gain 824 for the patient's current therapy plan may also be presented. The predicted FIM gain 824 may also be presented as the average value of the data representations of the other multiple patients similar to the data representation of the current patient based on the differentiation of the FIM score shown in upper two rows of the data representation. In addition to the predicted FIM gain 824, the predicted hospital days may also be presented as the average value of the data representations of the other multiple patients similar to the data representation of the current patient based on the number of rows of the data representation.

Figure 9:
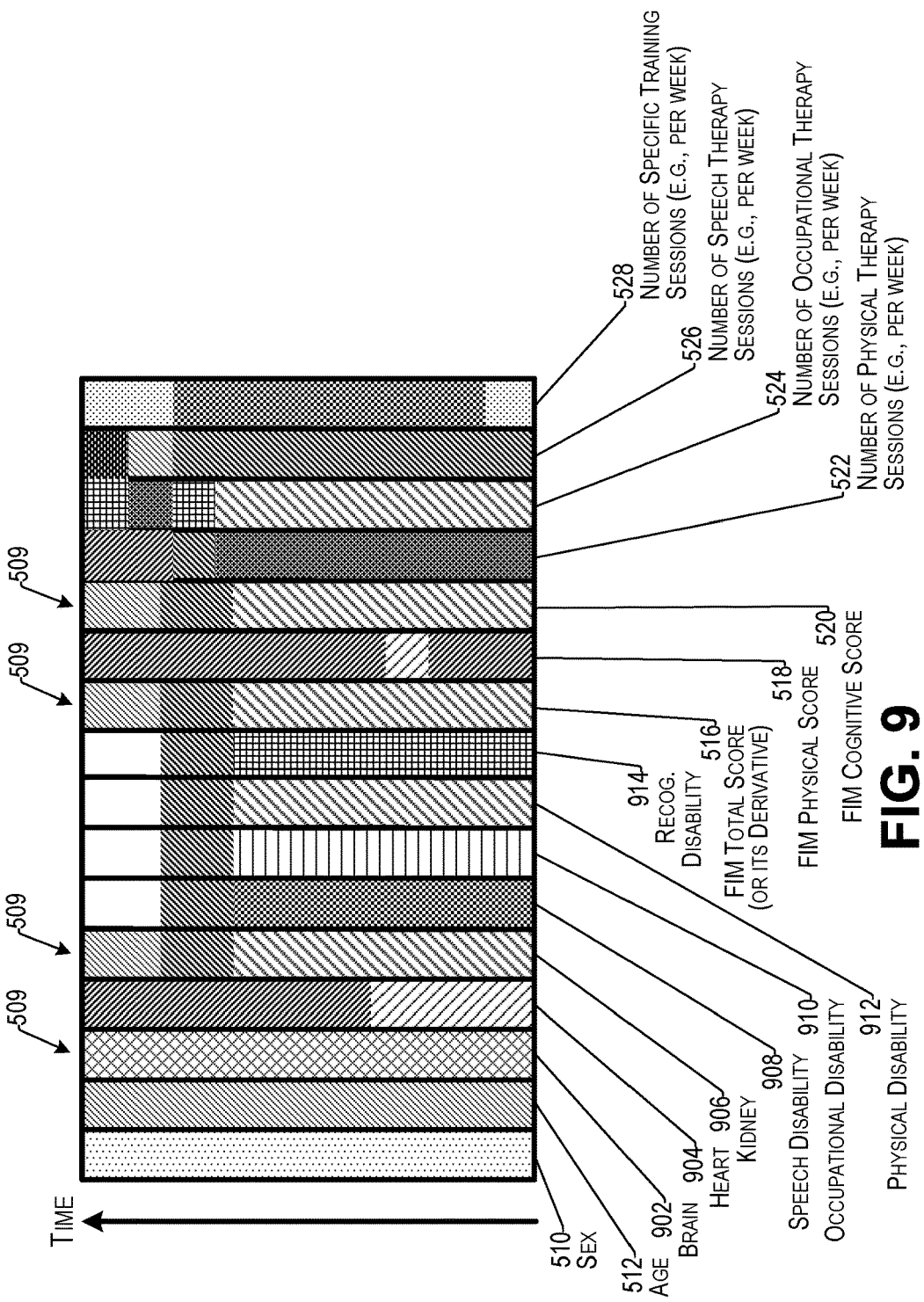
FIG. 9 illustrates an example data representation representing a patient medical record as an image according to some implementations.

FIG. 9 illustrates an example data representation 900 representing a patient medical record as an image according to some implementations. In this example, the data representation 900 includes 16 columns 509, rather than 10 columns as in the example of FIG. 5. For instance, in this example, the data representation 900 includes nine of the parameters discussed above, i.e., patient sex 510, age 512, FIM total score 516, FIM physical score 518, FIM cognitive score 520, number of physical therapy sessions 522, number of occupational therapy sessions 524, number of speech therapy sessions nine 526, and number of specific training sessions 528. In this example, the disease/disability parameter 514 from FIG. 5 is broken out into seven additional columns to describe specific diseases or disabilities. Thus in this example, the additional patient information parameters include a brain disease 902, a heart disease 904, a kidney disease 906, speech disability 908, occupational disability 910, physical disability 912, or recognition disability 914. Furthermore, while two examples of data representations that may represent patient data as image data have been presented and described herein, numerous other variations will be apparent to those of skill in the art having the benefit of the disclosure herein.

Figure 10:
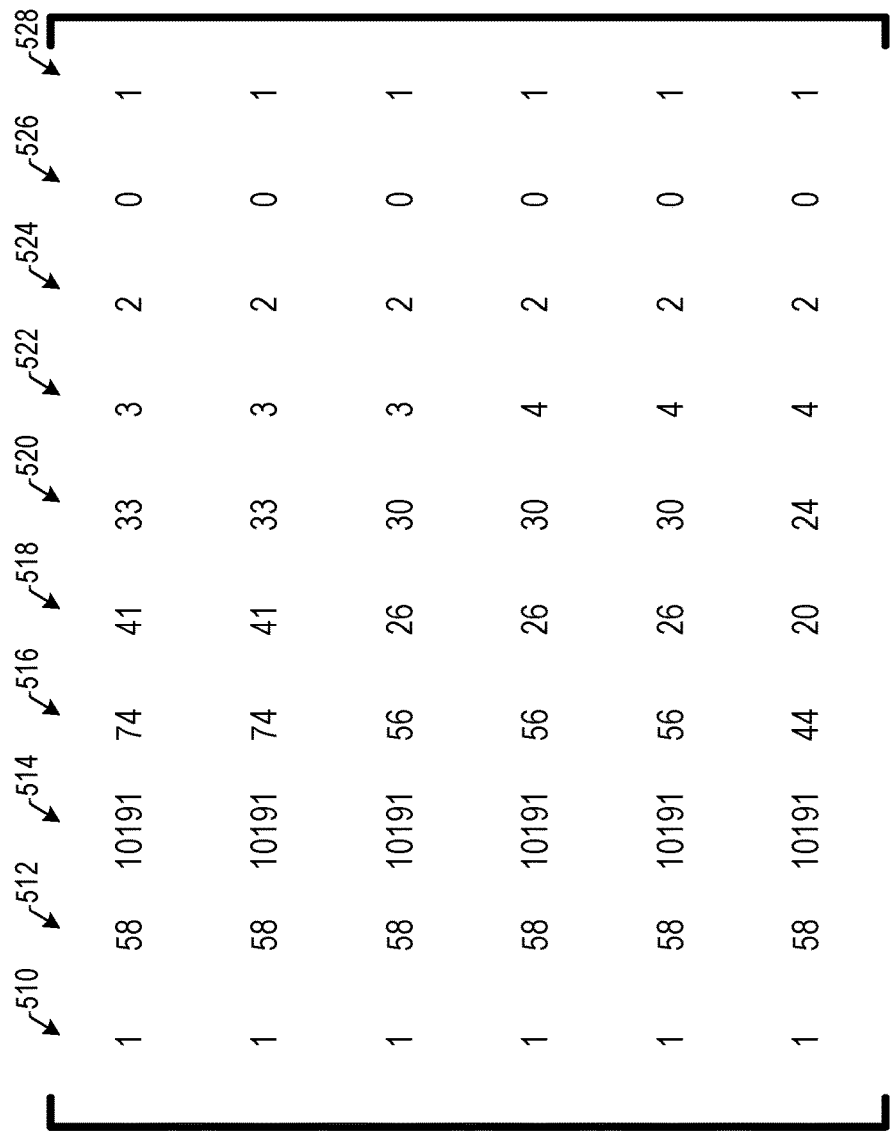
FIG. 10 illustrates a matrix-based data representation representing a patient medical record as a matrix according to some implementations.

FIG. 10 illustrates a matrix-based data representation 1000 representing a patient medical record as a matrix according to some implementations. In this example, rather than representing the patient data as image data in a data representation image, as in FIGS. 5 and 9, the patient data may be represented as a matrix with numeric values corresponding to the selected patient parameters. Accordingly, the columns may be the same as in the example of FIG. 5 and may include sex 510, age 512, disease or disability type DXIV, FIM total score 516, FIM physical score 518, FIM cognitive score 520, number of physical therapy sessions 522, number of occupational therapy sessions 524, number of speech therapy sessions 526, and number of specific training sessions 528 per time period. In the examples herein, the machine learning model may be trained using matrices rather than images, and the technique for appending alternative therapies may be similar to that discussed above with respect to FIG. 7. Consequently, implementations herein may apply a matrix-based data representation 1000 in a manner similar to that discussed above with respect to the image-based data representations 500 and 900.

FIG. 11 is a flow diagram illustrating an example process 1100 for using machine learning to determine a therapy plan according to some implementations. In some examples, the process 1100 may be executed by the analysis program 126 on the service computing device or other suitable computing device. In some examples, the process 1100 may incorporate some or all of the processes 200 and 700 discussed above.

At 1102, the analysis program may receive medical records for a plurality of patients, the medial records including therapy information and changes in a quantified disability status for individual ones of the patients.

At 1104, the analysis program may generate a plurality of data representations based on the medical records for the individual patients, each data representation representing a therapy performed and a quantified disability status of the individual patient. For instance, as discussed above, the data representation may be an image that summarizes selected parameters of the medical information of each patient, including an FIM score or other quantified disability status and one or more therapies that were applied to the patient.

At 1106, the analysis program may select a subset of the representations corresponding to an improvement in the quantified disability status exceeding a first threshold. For example, as discussed above with respect to FIG. 6, the analysis program may group the data representations into a plurality of subsets 600 (e.g., Patterns 1-4) based on FIM gain thresholds, e.g., an FIM gain of 10 points or greater for a first subset, an FIM gain from 5 to 9 points for a second subset, an FIM gain of 0-4 points for a third subset, and a negative FIM gain for a fourth subset. Further, while four subsets are described in some examples herein, in other examples, a different number of subsets and/or different thresholds and ranges for the subsets may be used.

At 1108, the analysis program may train a machine learning model based at least on the subset of the representations. For example, as discussed above, the analysis program may invoke the model building program to generate the machine learning model using at least the data representations in the first subset, i.e., the subset (Pattern 1) with the highest FIM gains.

At 1110, the analysis program may receive patient information for a first patient, the patient information including a current quantified disability status of the first patient.

At 1112, the analysis program may generate a first data representation from the patient information. For example, the analysis program may generate an image-based or matrix-based data representation to summarize a portion of the patient information, which may include FIM scores (or other quantified disability status of the patient) and therapies applied to the patient, as well as other patient information, as discussed above e.g., with respect to FIGS. 4, 5, 9, and 10.

At 1114, the analysis program may append, to the first data representation, therapies extracted from the subset of the representations to generate a plurality of the first representations with appended therapies. For example, as discussed above with respect to FIG. 7, the analysis program may append a plurality of different therapy patterns extracted from other data representations in the first subset to generate a plurality of the first data representations with the different therapy patterns.

At 1116, the analysis program may input the first data representation(s) to the machine learning model to compare the first data representation(s) with the data representations in the subset to determine at least one therapy plan predicted to provide an improvement in the current quantified disability status of the first patient. For example, the machine learning model may be configured to perform classification of the appended data representations to attempt to match the appended data representations with one or more representations in the first subset based on a probability of a match.

At 1118, the analysis program may perform at least one action based on the determined at least one therapy, the at least one action including at least one of: sending information related to the at least one therapy to a client device for presentation in a GUI by the client device; or sending a control signal to a therapy device to cause the therapy device to provide the at least one therapy to the patient. For example, as discussed above with respect to FIG. 1, a therapy device may be controlled directly by the analysis program based on the output of the machine learning model for applying a selected type of therapy to a patient. Additionally, or alternatively, the analysis program may send information on selected therapies and expected improvement in disability status of the patient to a medical professional or other user of the system, which may cause a client application to present the selected therapies in a GUI for review and application to the patient by the user.

The example processes described herein are only examples of processes provided for discussion purposes. Numerous other variations will be apparent to those of skill in the art in light of the disclosure herein. Further, while the disclosure herein sets forth several examples of suitable systems, architectures and environments for executing the processes, the implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Various instructions, processes, and techniques described herein may be considered in the general context of computer-executable instructions, such as programs stored on computer-readable media, and executed by the processor(s) herein. Generally, programs include routines, modules, objects, components, data structures, executable code, etc., for performing particular tasks or implementing particular abstract data types. These programs, and the like, may be executed as native code or may be downloaded and executed, such as in a virtual machine or other just-in-time compilation execution environment. Typically, the functionality of the programs may be combined or distributed as desired in various implementations. An implementation of these programs and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

The invention claimed is:

1. A system comprising:
one or more processors; and
one or more non-transitory computer-readable media maintaining executable instructions, which, when executed by the one or more processors, configure the one or more processors to perform operations comprising:
receiving medical records for a plurality of patients;
generating a plurality of data representations based on the medical records for individual ones of the patients, each data representation representing at least a therapy performed and a quantified disability status of the individual patient, each of the data representations being generated as an image including a plurality of blocks arranged in rows and columns, each block corresponding to a value of a patient information parameter, and removing, from each data representation, a set of blocks corresponding to most recent patient information prior to using the plurality of data representations as training data for a machine learning model, the patient information parameters including, in addition to therapy performed and the quantified disability status of the individual patient, at least one of disease type, disability type, patient age, patient sex, a time series of quantified disability statuses, a number of physical therapy sessions during a period, a number of occupational therapy sessions per during a period, a number of speech therapy sessions during a period, or a number of specific training sessions during a period;
grouping the data representations into a plurality of subsets based at least on an amount of improvement in a respective quantified disability status of the individual patient for a respective therapy performed in comparison to a quantified disability status of the individual patient prior to performance of the respective therapy;
selecting, as at least a portion of the training data, a subset of the data representations for which the amount of improvement in the quantified disability status exceeds a threshold indicating a highest amount of improvement as compared to other subsets of the plurality of subsets;
training the machine learning model using at least the plurality of the data representations in the selected subset as the training data;
receiving patient information for a first patient, the patient information including a current quantified disability status of the first patient;
generating at least a first data representation from the patient information for the first patient by appending at least one combination of therapy plans or options extracted from the data representations selected in an ascending order of a difference from the first data representation in the selected subset;
performing classification of the first data representation with the data representations in the subset based at least on using the machine learning model to determine whether the first data representation matches at least one of the data representations in the subset within a threshold probability for selecting at least one combination of therapy options predicted to provide a highest amount of expected improvement at a highest probability in the current quantified disability status of the first patient, wherein the at least one combination of therapy plans or options includes at least one of physical therapy, occupational therapy, speech therapy, or specific training; and
sending information related to the selected at least one combination of therapy plans or options, including the probability and the expected improvement of quantified disability status to a computing device to cause, at least in part, the computing device to present a graphical user interface including the selected at least one combination of therapy plans or options.

2. The system as recited in claim 1, wherein graphic effects applied to individual ones of the blocks in the image are selected based on the corresponding value of the patient information parameter.

3. The system as recited in claim 2, wherein:
a first plurality of the blocks represent patient quantified disability status determined over time; and
a second plurality of the blocks represent therapy received by the patient over time.

4. The system as recited in claim 2, the operations further comprising referring to a data structure for determining at least one of a color or graphic effect to apply to the blocks in the data representations, the data structure correlating patient information parameter values or ranges of values with specified colors and/or graphic effects.

5. The system as recited in claim 1, wherein performing the recognition on the first data representation comprises:
appending at least one combination of therapy plans or options extracted from at least one of the data representations in the selected subset to the first date representation; and
performing classification of the first data representation having appended therapy information by comparing a ratio of the data representations similar to the first data representation between each subset.

6. The system as recited in claim 1, the operations further comprising:
accessing a medical record data structure to generate the data representations as images representative of information contained in individual medical records;
storing the data representations in a training data data structure;
wherein training the machine learning model based at least partially on the plurality of the data representations in the subset includes accessing the stored data representations in the training data data structure.

7. The system as recited in claim 1, the operations further comprising:
extracting a plurality of therapy patterns from the data representations in the selected subset;
generating a plurality of the first data representations with respective therapy patterns of the plurality of therapy patterns appended to respective ones of the first data representations;
inputting the plurality of first data representations as inputs to the machine learning model to compare the plurality of first data representations with the data representations in the selected subset to determine a matched data representation in the selected subset having a probability of a closest match to a selected one of the first data representations having a therapy pattern appended; and
selecting at least one of the combination of therapy plans or options based on the therapy pattern appended to the selected one of the first data representations as a therapy plan for the first patient.

8. The system as recited in claim 7, wherein the operation of sending information related to the selected at least one combination of therapy plans or options, including the probability and the expected improvement of quantified disability status, to the computing device further comprises sending a control signal to a therapy device to cause the therapy device to apply the selected at least one combination of therapy plans or options to the first patient based on the therapy pattern appended to the selected one of the first data representations.

9. The system as recited in claim 1, the operations further comprising determining a predicted improvement in the quantified disability status for a current therapy plan of the first patent based on using the first data representation as an input to the machine learning model.

10. The system as recited in claim 1, the operations further comprising also generating the data representations as a matrix including a plurality of columns and rows of values corresponding to patient information parameter values.

11. The system as recited in claim 1, wherein the operation of sending information related to the at least one combination of therapy plans or options, including the probability and the expected improvement of quantified disability status, to a computing device comprises sending at least one of the combination of therapy plans or options determined based on the selected at least one combination of therapy plans or options to a client device to cause the client device to present the at least one combination of therapy plans or options in the graphic user interface along with a quantified predicted improvement in the quantified disability status of the first patient determined for the at least one combination of therapy plans or options.

12. A method comprising:
receiving, by one or more processors, medical records for a plurality of patients;
generating a plurality of data representations based on the medical records for individual ones of the patients, each data representation representing at least a therapy performed and a quantified disability status of the individual patient, each of the data representations being generated as an image including a plurality of blocks arranged in rows and columns, each block corresponding to a value of a patient information parameter, and removing, from each data representation, a set of blocks corresponding to most recent patient information prior to using the plurality of data representations as training data for a machine learning model, the patient information parameters including, in addition to therapy performed and the quantified disability status of the individual patient, at least one of disease type, disability type, patient age, patient sex, a time series of quantified disability statuses, a number of physical therapy sessions during a period, a number of occupational therapy sessions per during a period, a number of speech therapy sessions during a period, or a number of specific training sessions during a period;
grouping the data representations into a plurality of subsets based at least on an amount of improvement in a respective quantified disability status of the individual patient for a respective therapy performed in comparison to a quantified disability status of the individual patient prior to performance of the respective therapy;
selecting, as at least a portion of the training data, a subset of the data representations for which the amount of improvement in the quantified disability status exceeds a threshold indicating a highest amount of improvement as compared to other subsets of the plurality of subsets;
training the machine learning model using at least the plurality of the data representations in the selected subset as the training data;
receiving patient information for a first patient, the patient information including a current quantified disability status of the first patient;
generating at least a first data representation from the patient information for the first patient by appending at least one combination of therapy plans or options extracted from the data representations selected in an ascending order of a difference from the first data representation in the selected subset;
performing classification of the first data representation with the data representations in the subset based at least on using the machine learning model to determine whether the first data representation matches at least one of the data representations in the subset within a threshold probability for selecting at least one therapy predicted to provide a highest amount of expected improvement at a highest probability in the current quantified disability status of the first patient, wherein the at least one combination of therapy plans or options includes at least one of physical therapy, occupational therapy, speech therapy, or specific training; and
sending information related to the selected at least one combination of therapy plans or options, including the probability and the expected improvement of quantified disability status, to a computing device to cause, at least in part, the computing device to present a graphical user interface including the selected at least one combination of therapy plans or options.

13. One or more non-transitory computer-readable media storing instructions that, when executed by one or more processors of a system, program the one or more processors of the system to perform operations comprising:
receiving medical records for a plurality of patients;
generating a plurality of data representations based on the medical records for individual ones of the patients, each data representation representing at least a therapy performed and a quantified disability status of the individual patient, each of the data representations being generated as an image including a plurality of blocks arranged in rows and columns, each block corresponding to a value of a patient information parameter, and removing, from each data representation, a set of blocks corresponding to most recent patient information prior to using the plurality of data representations as training data for a machine learning model, the patient information parameters including, in addition to therapy performed and the quantified disability status of the individual patient, at least one of disease type, disability type, patient age, patient sex, a time series of quantified disability statuses, a number of physical therapy sessions during a period, a number of occupational therapy sessions per during a period, a number of speech therapy sessions during a period, or a number of specific training sessions during a period;
grouping the data representations into a plurality of subsets based at least on an amount of improvement in a respective quantified disability status of the individual patient for a respective therapy performed in comparison to a quantified disability status of the individual patient prior to performance of the respective therapy;

selecting, as at least a portion of the training data, a subset of the data representations for which the amount of improvement in the quantified disability status exceeds a threshold indicating a highest amount of improvement as compared to other subsets of the plurality of subsets;

training the machine learning model using at least the plurality of the data representations in the selected subset as the training data;

receiving patient information for a first patient, the patient information including a current quantified disability status of the first patient;

generating at least a first data representation from the patient information for the first patient by appending at least one combination of therapy plans or options extracted from the data representations selected in an ascending order of a difference from the first data representation in the selected subset;

performing classification of the first data representation with the data representations in the subset based at least on using the machine learning model to determine whether the first data representation matches at least one of the data representations in the subset within a threshold probability for selecting at least one therapy predicted to provide a highest amount of expected improvement at a highest probability in the current quantified disability status of the first patient, wherein the at least one combination of therapy plans or options includes at least one of physical therapy, occupational therapy, speech therapy, or specific training; and sending information related to the selected at least one combination of therapy plans or options, including the probability and the expected improvement of quantified disability status, to a computing device to cause, at least in part, the computing device to present a graphical user interface including the selected at least one combination of therapy plans or options.

14. The system as recited in claim 1, the operations further comprising extracting, from the selected subset of the data representations for which the amount of improvement in the quantified disability status exceeds the threshold indicating the highest amount of improvement, a plurality of combinations of therapy options containing data whose patient information, disease information, disability information, and/or quantified disability statuses are within a threshold difference of the first data representation generated from the patient information for the first patient.

15. The system as recited in claim 14, the operations further comprising:
   appending the extracted plurality of combinations of therapy options to the first data representation to create a plurality of new data representations; and
   using the machine learning model to perform pattern recognition on each of the plurality of new data representations so that combinations of therapy options recognized as patterns with a highest degree of improvement in the quantified disability status are output in descending order of probability for indicating therapy options having highest probability of success for the first patient.

16. The system as recited in claim 15, wherein a new row is added to a respective data representation for a respective patient when a new quantified disability status is determined for the respective patient.

17. The system as recited in claim 15, generating the respective data representations as respective images including multiple pixel bands arranged in a matrix to represent the patient information parameters by the multiple pixel bands.

18. The system as recited in claim 15, the operations further comprising referring to a data structure for determining at least one of a color or graphic effect to apply to the blocks in the data representations, the data structure correlating patient information parameter values or ranges of values with specified colors and/or graphic effects.

19. The method as recited in claim 12, further comprising extracting, from the selected subset of the data representations for which the amount of improvement in the quantified disability status exceeds the threshold indicating the highest amount of improvement, a plurality of combinations of therapy options containing data whose patient information, disease information, disability information, and/or quantified disability statuses are within a threshold difference of the first data representation generated from the patient information for the first patient.

20. The method as recited in claim 19, further comprising generating the respective data representations as respective images including multiple pixel bands arranged in a matrix to represent the patient information parameters by the multiple pixel bands.

* * * * *